United States Patent
Debski et al.

(10) Patent No.: US 11,891,648 B2
(45) Date of Patent: Feb. 6, 2024

(54) METHOD AND SYSTEM FOR RAPIDLY TESTING ANTIMICROBIAL SUSCEPTIBILITY

(71) Applicant: BACTEROMIC Sp. z o.o., Warsaw (PL)

(72) Inventors: Pawel Debski, Warsaw (PL); Piotr Garstecki, Warsaw (PL)

(73) Assignee: BACTEROMIC SP. Z O.O.

( * ) Notice: Subject to any disclaimer, the term of this patent is extended or adjusted under 35 U.S.C. 154(b) by 305 days.

(21) Appl. No.: 17/252,189

(22) PCT Filed: Jul. 16, 2019

(86) PCT No.: PCT/EP2019/069056
§ 371 (c)(1),
(2) Date: Dec. 14, 2020

(87) PCT Pub. No.: WO2020/016200
PCT Pub. Date: Jan. 23, 2020

(65) Prior Publication Data
US 2021/0254126 A1     Aug. 19, 2021

(30) Foreign Application Priority Data
Jul. 16, 2018   (EP) .................................. 18183741

(51) Int. Cl.
| C12Q 1/00 | (2006.01) |
| C12M 1/00 | (2006.01) |
| C12Q 1/20 | (2006.01) |
| C12M 1/36 | (2006.01) |
| C12M 1/34 | (2006.01) |

(52) U.S. Cl.
CPC ............... *C12Q 1/20* (2013.01); *C12M 41/36* (2013.01); *C12M 41/48* (2013.01)

(58) Field of Classification Search
CPC ............ C12Q 1/18; C12Q 1/20; C12M 41/36; C12M 41/48
See application file for complete search history.

(56) References Cited

U.S. PATENT DOCUMENTS

| 6,165,741 A | 12/2000 | Wilson et al. | .................. 435/34 |
| 6,265,182 B1 | 7/2001 | Kocagoz | ......................... 435/32 |

(Continued)

FOREIGN PATENT DOCUMENTS

| EP | 0 128 527 | 12/1984 | ............... C12Q 1/18 |
| EP | 1 466 985 | 10/2004 | ............... C12Q 1/04 |

(Continued)

OTHER PUBLICATIONS

Jorgensen et al. "Antimicrobial susceptibility testing: a review of general principles and contemporary practices." Clinical infectious diseases 49.11 (2009): 1749-1755 (Year: 2009).*

(Continued)

*Primary Examiner* — Nathan A Bowers
(74) *Attorney, Agent, or Firm* — HAYES SOLOWAY P.C.

(57) ABSTRACT

Disclosed are methods and systems for rapidly testing antimicrobial susceptibility, wherein the qualitative and quantitative susceptibility of an inoculated microorganism against an antimicrobial agent or a combination of antimicrobial agents is determined as a function of one or more slopes of linear trends α of data of readouts.

20 Claims, 7 Drawing Sheets

(56) References Cited

U.S. PATENT DOCUMENTS

| | | | |
|---|---|---|---|
| 6,611,765 B2 | 8/2003 | Boeufgras et al. | 702/19 |
| 6,649,402 B2 | 11/2003 | Van der Weide et al. | 435/288.4 |
| 2016/0289729 A1 | 10/2016 | Richards et al. | C12Q 1/025 |
| 2018/0179572 A1 | 6/2018 | Stern et al. | C12Q 1/18 |
| 2021/0016274 A1 | 1/2021 | Garstecki et al. | B01L 3/50273 |
| 2021/0023553 A1 | 1/2021 | Garstecki et al. | B01L 3/5027 |

FOREIGN PATENT DOCUMENTS

| | | | |
|---|---|---|---|
| PL | 425106 | 10/2019 | B01L 3/00 |
| PL | 425107 | 10/2019 | B01L 3/00 |
| WO | WO 96/12819 | 5/1996 | C12Q 1/02 |
| WO | WO 02/083935 | 10/2002 | C12Q 1/18 |

OTHER PUBLICATIONS

International Search Report and Written Opinion issued in PCT/EP2019/069056, dated Aug. 23, 2019, 9 pages.

International Preliminary Report on Patentability issued in PCT/EP2019/069056, dated Jan. 19, 2021, 6 pages.

Axén N. et al. "Friction and Wear Measurement Techniques", 2001, CRC Press LLC, 18 pages.

Baltekin O., et al., "Antibiotic susceptibility testing in less than 30 min using direct single-cell imaging" PNAS, Aug. 22, 2017, vol. 114, No. 34, pp. 9170-9175, 6 pages.

Bartlett, J. M. S.; Stirling, D. (2003). "A Short History of the Polymerase Chain Reaction". PCR Protocols. Methods in Molecular Biology. 226 (2nd ed.). pp. 3-6, 4 pages.

Chorianopoulos et al., "A newly developed assay to study the minimum inhibitory concentration of Satureja spinosa essential oil" *Journal of Applied Microbiology*, 100, (2006) 778-786, 10 pages.

Corning® 96 Well CellBIND® Microplate, https://www.sigmaaldrich.com/catalog/product/sigma/cls3340, 2021, 2 pages.

Corning™ Costar™ Flat Bottom Cell Culture Plates, https://www.fishersci.com/shop/products/costar-cell-culture-plates-17/0720090, accessed Feb. 24, 2021, 2 pages.

Eisenberg et al., "Why Is the Sum of Independent Normal Random Variables Normal?" *Mathematics Magazine*, vol. 81, No. 5, Dec. 2008, 362-366, 5 pages.

CLSI Performance Standards for Antimicrobial Susceptibility Testing, 22th Edition; CLSI document M100-S22. Wayne, PA: Clinical and Laboratory Standard Institute; 2012, 188 pages.

EUCAST European Committee on Antimicrobial Susceptibility Testing (http://www.eucast.org), Jun. 2020, 4 pages.

Huggett, J. F. et al., Considerations for digital PCR as an accurate molecular diagnostic tool, Clinical Chemistry, 61 (1), 79-88, 2015, 10 pages.

Lambert et al., "Susceptibility testing: accurate and reproducible minimum inhibitory concentration (MIC) and non-inhibitory concentration (NIC) values" *Journal of Applied Microbiology*, 88 (2000) 784-790, 7 pages.

Lambert et al., "A model for the efficacy of combined inhibitors" *Journal of Applied Microbiology*, 95 (2003) 734-743, 10 pages.

Morley, A.A . . . Digital PCR: A brief history. Biomolecular Detection and Quantification, 1(1):1-2, 2014, 2 pages.

Notomi T et al., (2000). "Loop-mediatedisothermal amplification of DNA". Nucleic Acid Res. 28(12): E63, 7 pages.

Schoepp N., et al., "Rapid pathogen-specific phenotypic antibiotic susceptibility testing using digital LAMP quantification in clinical samples" Science Translational Medicine 9, Oct. 4, 2017, 12 pages.

Schmitz, T. et al. "Wear-Rate Uncertainty Analysis", Journal of Tribology, vol. 126, Oct. 2004, 802-807, DOI: 10.1115/1.1792675, 7 pages.

Zwietering, et al . . . (1990), "Modeling of the Bacterial Growth Curve", Applied and Environmental Microbiology, 56 (6): 1875-1881, 7 pages.

\* cited by examiner

METHOD AND SYSTEM FOR RAPIDLY TESTING ANTIMICROBIAL SUSCEPTIBILITY

TECHNICAL FIELD

The present invention relates to methods and systems for rapidly testing antimicrobial susceptibility, wherein the qualitative and quantitative susceptibility of an inoculated microorganism against an antimicrobial agent or a combination of antimicrobial agents is determined as a function of one or more slopes of linear trends α of readouts values.

BACKGROUND ART

In clinical microbiology, phenotypic investigation by liquid culture is a gold standard for assessing the resistance of samples of in particular bacterial or fungal microorganisms to one or more antimicrobials. One method relates to phenotypic Antimicrobial Susceptibility Testing (AST), which, e.g., involves incubating one or more isolates of the microorganisms respectively in liquid media in the presence of one or a combination of two or more antimicrobials and assessing whether growth of the respective isolate population occurs.

The Antimicrobial Susceptibility Testing allows for qualitative determination whether the isolate of the microorganism is SUSCEPTIBLE (S), INTERMEDIATE (I) or RESISTANT (R) with respect to the antimicrobials used:

Thereby the category SUSCEPTIBLE indicates that the antimicrobial/combination of antimicrobials may be an appropriate choice for treating the infection caused by the microorganism tested and bacterial/fungal resistance is absent or at a clinically insignificant level.

The category INTERMEDIATE indicates that the tested isolate populations of the microorganism are "moderately susceptible" to the tested antimicrobial, whereby this category serves as a buffer zone between SUSCEPTIBLE and RESISTANT. Antimicrobials falling in this category may still be indicated in case they can be concentrated at the focus of infection (e.g., quinolones and β-lactam in urine) or when a higher than normal dosage of the antimicrobial can be used (e.g., β-lactam) because of its low toxicity. The antimicrobial agent may still be effective against the tested isolate but response rates may be lower than for susceptible isolates.

The category RESISTANT indicates that the tested isolate is resistant to the respective antimicrobial, which means that the bacterial or fungal microorganism does not seem to be inhibited by the usually achievable concentrations of the tested antimicrobial agent with normal dosage schedules. Thus, antimicrobials of this category are not appropriate choice for treating the infection caused by the bacterial or fungal isolate tested.

Alternatively, the Wild type (WT) or Non Wild type (NWT) may be used to categorize the susceptibility of the microorganism. Accordingly, a microorganism isolate may be defined as WT for a species by the absence of phenotypically detectable acquired and mutational resistance mechanisms to the antimicrobial agent in question. This means in turn, that a microorganism isolate may be defined as NWT for a species by the presence of phenotypically detectable acquired or mutational resistance mechanisms to the antimicrobial agent in question.

In addition, the Antimicrobial Susceptibility Testing method allows for a quantitative evaluation by determining the minimum inhibitory concentration (MIC) of an antimicrobial for the particular isolate, whereby an antimicrobial dilution assay is conducted in agar, within culture tubes or within microtitre plates. When determining the MIC within culture tubes or microtitre plates, serial dilutions of a single antimicrobial or a combination of two or more antimicrobials are inoculated into the well or tube alongside a standard inoculum of a sample microorganism. Growth in the presence of the respective antimicrobial concentration is measured using turbidity. Minimum inhibitory concentration refers to the highest dilution or lowest concentration of antimicrobial that completely inhibits growth of the isolate. When using the MIC method on agar, e.g., an inoculated diffusion strip containing an antimicrobial concentration gradient is applied to the agar so that the gradient transfers from the strip into the agar. After overnight incubation or longer, an elliptical zone of inhibition centered around the strip is formed. The MIC value can be read at the point the ellipse edge intersects the MIC strip. The resulting MIC value can then be interpreted using standards such as provided by European Committee on Antimicrobial Susceptibility testing (EUCAST) or Clinical & Laboratory Standards Institute (CLSI).

In view of the threats posed by, possibly lethal, infections caused by antimicrobial resistant microorganisms and the increase of worldwide spread of bacterial resistance to antibiotics, rapid detection of such resistant species, and determination of minimum inhibitory concentrations is increasingly desired.

Although phenotypic assays of antimicrobial resistance are very reliable, many of them are also very time consuming, as the proliferation rate of the microorganisms in particular slows down when an isolate of the microorganism has been inoculated into the new culture medium, which can be observed as so-called lag phase of bacterial growth in batch culture. In this phase standard measurement methods used to enumerate microorganisms yield unacceptably low signal to noise ratio. The prior art of Antimicrobial Susceptibility Testings, however, determines whether an isolate of the microorganism does or does not proliferate in a particular environment only in the later growth phases, e.g. in the exponential or log phase. Thus, the minimum time for phenotypic Antimicrobial Susceptibility Testing depends on the exponential or log growth phases of the microorganism. According to FDA, for fast-growing bacteria, tests with incubation times lower than 16 hours are referred to as employing "short-term incubation", however, usually incubation times of 16 to 20 h (with some exception) are required, so that the overall results of the Antimicrobial Susceptibility Testing takes up to days and weeks. In view that the qualitative and quantitative assessment of AST is sometimes time critical for live threatening infections, it would be desirable to shorten the time for obtaining the qualitative and quantitative AST results.

One way of speeding up the time for providing qualitative and/or quantitative results of the AST is by using microtitre plate culturing, such as in standard 96- or 384-well microtitre plates, which enables simultaneously applying multiple different conditions, such as presence or absence of specific antimicrobials or different concentrations thereof to the same sample of microorganism. Potential growth, i.e. multiplication of microorganism, takes place in the wells of the microtitre plates and is either optically assessed by eyes or is assessed by machine measurement of physical or chemical properties which directly depend on the growth of the microorganisms.

Another attempt to speed up antimicrobial resistance detection and quantification is the automation of culture.

Examples of automated Antimicrobial Susceptibility Testing systems are VITEK and Phoenix (offered by bioMerieux and Becton Dickinson, respectively), which take advantage of dedicated microfluidic chips, or MicroScan and Sensititre, both handling 96-well microtitre plates.

In addition, the prior art teaches to properly monitor the microbial culture in order to shorten the time needed for detection of its growth. These methods require measurement of specific physical or chemical properties of culture, usually under special conditions. By way of example, the colour of a culture medium (U.S. Pat. No. 6,265,182 B1), fluorescence quenching with the use of particular chemical compound (U.S. Pat. No. 6,165,741 B1), electrical impedance of small sample sub-volumes (U.S. Pat. No. 6,649,402 B2) or partial pressure of oxygen (EP 0 128 527 A2) are properties, which provide monitoring information on the growth of the microorganisms. Main drawback of these solutions is a requirement for specific experimental setup for measurements. In addition, the aforementioned methods do not enable conducting very fast assay (for example with the use of U.S. Pat. No. 6,265,182 B1 the antibiotic susceptibility test still takes 4 to 6 hours).

On the other hand significant progress in microfluidic techniques provides a way for very rapid AST assays. In article *Antibiotic susceptibility testing in less than 30 min using direct single-cell imaging* (O. Baltekin et al., PNAS Aug. 22, 2017, 114 (34), 9170-9175) such method is described where single bacteria can be trapped in microfluidic channels, treated with different media (i.e. with antibiotic or without it) and then observed by means of phase contrast microscopy. Influence of an antibiotic on a sample can also be rapidly detected according to the method disclosed in *Rapid pathogen-specific phenotypic antibiotic susceptibility testing using digital LAMP quantification in clinical samples* (Schoepp et al., Sci. Transl. Med. 9, eaal3693 (2017)). There, comparison between sample exposed to an antibiotic and reference is made based on a result of quantitative assay based on nucleic acid isothermal amplification. Both microfluidic technique methods give impressive parameters of an assay, but they require also very sophisticated equipment.

In conclusion, the state-of-art solutions are characterized by the following problems:
- The standard antimicrobial susceptibility testing is in view of the incubation step for conducting growth of the isolated microorganism sample very time consuming.
- Measurements based on impedance/colour/fluorescence quenching require specific experimental set-up.
- The new microfluidic technique described by Baltekin et al. observes single bacteria, therefore it scales down the observed system and also requires specific set-up and laboratory routines.
- The new microfluidic technique described by Schoepp et al. also requires the use of specific laboratory routines (LAMP amplification).

BRIEF DESCRIPTION OF THE INVENTION

One or more problems of the present invention is/are solved by the subjects of the independent claims. Advantages (preferred embodiments) are set out in the detailed description hereinafter and/or the accompanying figures as well as in the dependent claims.

Accordingly, a first aspect of the present invention relates to a computer-implemented method for determining the qualitative or quantitative susceptibility of a microorganism inoculum in a phenotypic antimicrobial susceptibility test (AST) using broth dilution, characterized in that the AST method comprises or consists of the following steps:

a) Providing a microorganism inoculum and diluting the inoculum in a medium suitable for broth dilution AST, b) Providing a carrier comprising one or more compartments suitable for broth dilution AST, wherein the or at least part of the compartments comprise respectively a single antimicrobial agent or a combination of antimicrobial agents, c) Dispensing a sample of the medium containing the diluted inoculum of step a) into the or at least part of the compartments of the carrier of step b) so that the one or more inoculated compartments of the carrier comprise the respective test assays, d) Incubating the carrier of step c) comprising the respective one or more test assays, e) Measuring, during the incubation step d), at least n times for each of the one or more test assays with a constant or inconstant frequency $f$ a signal derived from a chemical or physical property of the inoculated microorganism, wherein the signal represents an essentially monotonic function of the number of the microorganisms in the measured test assay, and reading out corresponding values $\{x_i\}$ at corresponding recording times $\{t_i\}$, wherein i represents the index number of the measurement represented by an integer 1 to n, and wherein n represents a full integer of 13 or more measurements, f) Estimating one or more slopes of linear trends $\alpha$ in data as a function of distribution of a difference from a subtraction of constituents of a pair of the readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times 43 are used for the distribution, and g) Determining the qualitative or quantitative susceptibility of the inoculated microorganism against the single antimicrobial agent or the combination of antimicrobial agents as a function of one or more slopes of linear trends $\alpha$.

A second aspect of the present invention relates to a rapid antimicrobial susceptibility testing system for performing a phenotypic antimicrobial susceptibility test (AST) using broth dilution, the system comprising:

a) an incubation assembly adapted to house at least one carrier having one or more compartments for receiving a sample of a microorganism inoculum diluted in a growth medium, wherein the or at least part of the compartments comprise respectively a single antimicrobial agent or a combination of antimicrobial agents, so that each inoculated compartment houses a respective test assay, wherein the incubation assembly is configured to provide an incubation and/or measuring environment of the one or more test assays in the one or more compartments, b) an interrogation and readout assembly comprising interrogation means and measuring means configured to interrogate and readout the one or more test assays during incubation of the one or more carriers, wherein the interrogation and readout assembly facilitates i) measuring at least n times for each of the one or more test assays, with a constant or inconstant frequency $f$, a signal derived from a chemical or physical property of the inoculated microorganism, wherein the signal represents an essentially monotonic function of the number of the microorganisms in the measured test assay, and ii) reading out corresponding values $\{x_i\}$ at corresponding recording times $\{t_i\}$, wherein i represents the index number of the measurement represented by an integer 1 to n, wherein n represents a full integer of 13 or more measurements, and c) a computing assembly comprising one or more processors and one or more computer-readable media storing instructions that, when executed by the one or more processors, cause the one or more processors to perform operations comprising i) receiving from the interrogation and readout assembly the number n of readouts, the values $\{x_i\}$ and corresponding recording times $\{t_i\}$ and ii) estimating one or more slopes of linear trends α in data as a function of distribution of a difference from a subtraction of constituents of a pair of readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times 43 are used for the distribution, and iii) determining the qualitative or quantitative susceptibility of the inoculated microorganism against the single antimicrobial agent or the combination of antimicrobial agents as a function of one or more slopes of linear trends α.

A third aspect of the present invention relates to a use of the inventive rapid antimicrobial susceptibility testing system for performing a phenotypic antimicrobial susceptibility test (AST) using broth dilution in determining qualitative and quantitative susceptibility of an inoculated microorganism.

The inventive aspects of the present invention as disclosed hereinbefore can comprise—in case it is reasonable for a person skilled in the art any possible combination of the preferred inventive embodiments as set out in the dependent claims or disclosed in the following detailed description.

DETAILED DESCRIPTION OF THE INVENTION

Figure 1:
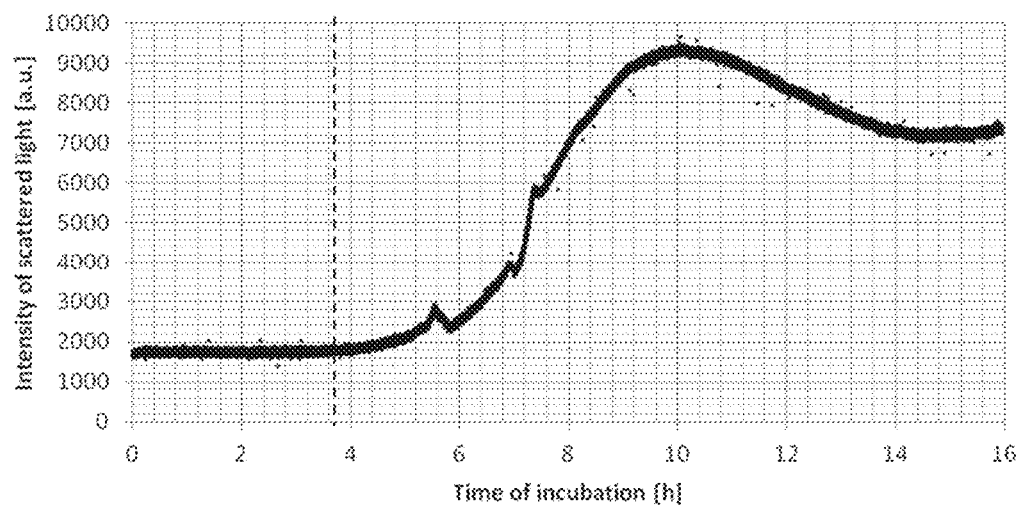
FIG. 1 shows an exemplary growth curve of a sample inoculated microorganism in an antimicrobial susceptibility test, where a dashed line indicates the end of the phase of growth wherein the changes of measured signal value due to the microbial population growth are smaller than the changes of the signal value due to the high-frequency noise of the measuring means.

As described in detail below, the present inventors have unexpectedly found out that when using the inventive method, system or use it is possible to reduce the incubation time of a standard antimicrobial susceptibility test (AST) using broth dilution and/or to increase the precision of the qualitative or quantitative determination of antimicrobial susceptibility. Such improvements are achieved without the use of specific experimental set up and laboratory routines, as required for measurements of the prior art, e.g., measurements based on impedance, colour, fluorescence quenching or the microfluidic techniques described by Baltekin et al. or Schoepp et al., where either a single bacterium is observed and the observed system is scaled down or LAMP amplification is used.

The present invention is based on an assessment of the distribution of a difference of a subtraction of constituents of a pair of read out values divided by the time interval between taking the read out values for 13 or more measurements of a test assay and determining the qualitative or quantitative antimicrobial susceptibility of the inoculated microorganism.

The inventive method is computer-implemented, which means, that the inventive method is carried out by use of a suitable processing means and optionally suitable storing means, e.g., by use of a computer, laptop, smart device etc., and in case assembly is connected to the internet, the suitable processing means and optionally storing means may be provided by an internet accessible server, in particular a cloud server network.

According to the present invention, part or all of the n readout values $\{x_i\}$, but at least 13 or more, preferably 100 or more, more preferably 500 or more, even more preferably 1000 or more readout values $\{x_i\}$ at corresponding n recording times 43 are used to estimate one or more slopes of linear trends $\alpha$ in data as a function of distribution of a difference from a subtraction of constituents of a pair of the readout values $\{x_i\}$ and $\{x_j\}$, where j>i, divided by the time interval $\delta t_{ij}$ between taking readouts indexed i and j. In other words, for at least 13 or more, preferably 100 or more, more preferably 500 or more, even more preferably 1000 or more readout values $\{x_i\}$ a distribution of a subtraction of constituents of a pair of the readout values divided by the time interval between the readouts (frequency $f$) can be calculated as follows:

From the set of n readout values $\{x_i\}$ (synonymously also referred to as readouts or readouts $\{x_i\}$), a set of $$\frac{n(n-1)}{2}$$

normalized differences $\{\eta_{ij}\}$ of a pair of readout values $$\eta_{ij} = \frac{x_j - x_i}{\delta t_{ij}},$$

where j>i, and $\delta t_{ij}$ is the time difference between taking readouts indexed i and j, may be constructed. If the readouts are taken with constant frequency, then $\delta t_{ij} = \delta t(j-i)$, where $\delta t$ is the average time between consecutive readouts.

The average difference $\bar{\eta}$ of all normalized differences $$\bar{\eta} = \frac{\sum_{j=2}^{n}\left(\sum_{i=1}^{j}\eta_{ij}\right)}{\frac{n(n-1)}{2}}$$

may be calculated. The average difference is equal to the estimate a of the slope of the series of readouts $\alpha$: $\bar{\eta}=\hat{\alpha}$. The inaccuracy $\sigma_\alpha$ of estimation of $\alpha$ is equal to $$\sigma_\alpha = \sqrt{\frac{4}{3}\frac{\pi\sigma}{\delta t}}n^{-\frac{3}{2}},$$

where $\sigma$ is the standard deviation of the high frequency noise of the instrument.

According to all aspects of the present invention the qualitative or quantitative susceptibility of the inoculated microorganism against the single antimicrobial agent or the combination of antimicrobial agents is determined as a function of one or more slopes of linear trends $\alpha$.

The determination of the qualitative or quantitative susceptibility of the inoculated microorganism is based on the finding, whether the growth of the inoculated microorganism is inhibited or not. Accordingly, the growth rate $\mu$ of the inoculated microorganism in the test assay y may be calculated using a calibration function $f(y)$: $\mu=(f'(y))^{-1}\cdot\alpha$.

The inaccuracy $\sigma_\mu$ of estimation of growth rate $\mu$ is equal to $|f'(y)|^{-1}\cdot\sigma_\alpha=|f'(y)|^{-1}\cdot$ $$\sqrt{\frac{4}{3}\frac{\pi\sigma}{\delta t}}n^{-\frac{3}{2}},$$

where $\sigma$ is the standard deviation of the high frequency noise of the instrument.

This means that the precision of the qualitative or quantitative susceptibility determination (i.e. standard deviation $\sigma_\alpha$) of an estimation of the linear trend $\alpha$ depends only on the number of readouts used for the distribution of subtraction and the standard deviation of high frequency noise from the measuring means a. Moreover it is proportional to $$n^{-\frac{3}{2}} = \left(n^{-\frac{1}{2}}\right)^3,$$

which means that the precision of the determination of the qualitative or quantitative susceptibility of the sample of inoculated microorganism increases faster with growing number of readouts than in the usual AST methods according to the prior art, e.g. least square method, where a scaling factor is $$n^{-\frac{1}{2}}.$$

Thus, according to the first aspect of the present invention the computer-implemented method for determining the qualitative or quantitative susceptibility of a microorganism inoculum in a phenotypic antimicrobial susceptibility test (AST) using broth dilution comprises or consists of the following steps:

a) Providing a microorganism inoculum and diluting the inoculum in a medium suitable for broth dilution AST, b) Providing a carrier comprising one or more compartments suitable for broth dilution AST, wherein the or at least part of the compartments comprise respectively a single antimicrobial agent or a combination of antimicrobial agents, c) Dispensing a sample of the medium containing the diluted inoculum of step a) into the or at least part of the compartments of the carrier of step b) so that the one or more inoculated compartments of the carrier comprise the respective test assays, d) Incubating the carrier of step c) comprising the respective one or more test assays, e) Measuring, during the incubation step d), at least n times for each of the one or more test assays with a constant or inconstant frequency $f$ a signal derived from a chemical or physical property of the inoculated microorganism, wherein the signal represents an essentially monotonic function of the number of the microorganisms in the measured test assay, and reading out corresponding values $\{x_i\}$ at corresponding recording times $\{t_i\}$, wherein i represents the index number of the measurement represented by an integer 1 to n, and wherein n represents a full integer of 13 or more measurements, f) Estimating one or more slopes of linear trends α in data as a function of distribution of a difference from a subtraction of constituents of a pair of the readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times $\{t_i\}$ are used for the distribution, and g) Determining the qualitative or quantitative susceptibility of the inoculated microorganism against the single antimicrobial agent or the combination of antimicrobial agents as a function of one or more slopes of linear trends α.

According to the present invention the antimicrobial susceptibility of any suitable microorganism can be tested, preferably the microorganism is selected from the list consisting of bacterium, e.g. aerobic or anaerobic bacterium including *mycobacterium*, and fungus. According to one embodiment of the present invention the microorganism is selected from the group consisting of bacterium including aerobic bacterium or anaerobic bacterium.

With respect to the first aspect, the microorganism inoculum and suitable broth dilutions for the respective microorganism are prepared according to standard methods in the art, in particular as described by EUCAST (The European Committee on Antimicrobial Susceptibility Testing; http://www.eucast.org.) and CLSI (Performance Standards for Antimicrobial Susceptibility Testing, 22th Edition; CLSI document M100-S22. Wayne, PA: Clinical and Laboratory Standard Institute; 2012). The respective described standard methods for antimicrobial susceptibility testing for bacteria, mycobacteria and fungus are incorporated herein with reference. According to the present invention the microorganism inoculum, which is usually an overnight culture, or a portion of an overnight culture, of a tested microorganism is diluted in a suitable growth medium, such as the liquid broth dilution (also synonymously also referred to as "medium suitable for broth dilution AST"). A sample of this diluted inoculum (synonymously also referred to as "a sample of the medium containing the diluted inoculum", "a sample of broth dilution of a microorganism inoculum" or "a sample of a microorganism inoculum diluted in a growth medium") is then used in step c) of the inventive method. According to Example 1, this suspension is further diluted twice by mixing with the respective solution of antibiotic in broth. With respect to the sample, the count of microorganism cells in the dilution is determinable. Preferably, the density of the sample medium containing the diluted inoculum is $5*10^5$ CFU/ml (Colony Forming Units/ml). In particular when testing bacteria as microorganisms, the broth is selected from un-supplemented cation-adjusted Mueller-Hinton broth (MH broth), which is used for testing of non-fastidious organisms according to the ISO standard 20776-1, 2006, or cation-adjusted MH broth supplemented with 5% lysed horse blood and 20 mg/L β-NAD (MH-F broth), which is used for testing *Streptococcus* spp. (including *S. pneumoniae*), *Haemophilus influenzae, Moraxella catarrhalis, Listeria monocytogenes, Campylobacter jejuni* and *coli, Pasteurella multocida, Corynebacterium* spp., *Aerococcus sanguinicola* and *urinae, Kingella kingae* and several other fastidious organisms. Un-supplemented MH broth may also be purchased from commercial sources.

According to the first aspect of the present invention, any suitable carrier comprising one or more compartments suitable for broth dilution AST, wherein the or at least part of the compartments comprise respectively a single antimicrobial agent or a combination of antimicrobial agents, can be used.

The carrier also generally facilitates measurement of the properties in step e) of the first inventive aspect as well as avoidance of cross contamination between the test assays. Such a carrier may be selected from the group consisting of microtiter plate, tube, e.g. Eppendorf tube, petri dish or microfluidic chip. The carrier represents preferably a microtiter plate or a microfluidic chip, as multiple test assays can be incubated simultaneously. A microfluidic chip may be still preferred as carrier according to all inventive aspects, as it may house equal to or greater than 100 incubation compartments, preferably equal to or greater than 128 incubation compartments, more preferably equal to or greater than 320 incubation compartments, even more preferably equal to or greater than 640 incubation compartments, and more preferably equal to or greater than 1280 incubation compartments. The (incubation) compartment of a microfluidic chip may synonymously also be referred to as incubation segment or incubation well. The carrier to be used for the present invention may also comprise means for facilitating incubation, such as temperature adjusting means and/or means for exchange of gases. Very preferred microfluidic chips suitable for the present invention are described in particular in Polish patent applications PL 425106 and PL 425107 (both in the name of Bacteromic sp. z.o.o., also the present applicant) and the content concerning the microfluidic chip of both applications PL 425106 and PL 425107 are incorporated herein by reference.

The one or more compartments of the carrier to be inventively used respectively comprise a single antimicrobial agent or a combination of two, three, four or more antimicrobial agents and optionally further excipients as necessary. The antimicrobial agent (synonymously also referred to as "antimicrobial") or combination of antimicrobial agents may be selected from the group of agents inhibiting the growth of bacteria, in particular mycobacteria, and/or fungi. In particular the antimicrobial agent or the combination of antimicrobial agents may comprise a bacteriostatic agent, a bactericide agent, a fungistatic agent or a fungicide agent. The single antimicrobial agent or the combination of antimicrobial agents and optionally the further excipients are dispensed into the respective compartments of the carrier by suitable means, wherein the final concentration of the antimicrobial agent(s) in the respective compartment must be known or determinable. In particular, in case a microtiter plate or a microfluidic chip is used, the single antimicrobial agent or the combination of two or more antimicrobial agents and optional further excipients are e.g. spotted into the respective compartments (wells of the microtiter plate or incubation compartments/segments/wells of a microfluidic chip). In case the antimicrobial agent is admixed with the inoculated microorganism in the dilution ration 1:1, then the concentration of the antimicrobial agent in the respective compartment must be twice as high as the target concentration. For example, equal portions (i.e., 100 µl or 50 µl) of the inoculated broth dilution and the antimicrobial agent dilution are admixed in a well of a multitier plate (e.g., Corning® 96 Well CellBIND® Microplate, https://www.sigmaaldrich.com/catalog/product/sigma/cls3340, Corning™ Costar™ Flat Bottom Cell Culture Plates, https://www.fishersci.com/shop/products/costar-cell-culture-plates-17/0720090) that allows for the measurement of optical properties of the sample. Preferably 3 repetitions for each test assay are prepared. When using other mixing ratios, then the respective antimicrobial agent concentration needs to be used. In case a quantitative determination of antimicrobial susceptibility, in particular the minimum inhibitory concentration shall be determined with the present invention, two or more compartments of the carrier comprise different concentrations of the single antimicrobial agent or the combination of antimicrobials. Preferably, the series of different concentrations is used in accordance with the standards provided by EUCAST (The European Committee on Antimicrobial Susceptibility Testing; http://www.eucast.org.) and CLSI (Performance Standards for Antimicrobial Susceptibility Testing, 22th Edition; CLSI document M100-S22. Wayne, PA: Clinical and Laboratory Standard Institute; 2012).

According to the first aspect of the present invention, a sample of the medium containing the diluted inoculum of step a) is dispensed into the or at least part of the compartments of the carrier of step b) so that the one or more inoculated compartments of the carrier comprise the respective test assays. The dispensing step may be conducted according to any suitable method according to the state of the art, in particular comprising dispensing means for manual or automated dispensing. Dispensing may also be facilitated by a microfluidic chip, wherein the microfluidic chip comprises a reservoir housing the sample of inoculated broth, wherein the reservoir is connected with the one or more compartments. The one or more compartments (incubation compartments/segments/wells) may be filled with a suitable amount of the inoculated broth by placing the microfluidic chip with the filled reservoir into a filling chamber and increasing pressure therein so that the inoculated broth dilution is pressed into the one or more compartments. A suitable microfluidic chip is disclosed in Polish patent applications PL 425106 and PL 425107.

According to the first aspect of the present invention, the carrier comprising the respective one or more test assays is incubated generally by using a suitable incubation assembly. The incubation assembly also disclosed with respect to the second aspect of the present invention is configured to provide a suitable incubation and/or measuring environment for the test assays of the one or more carriers contained therein. In the context of the present invention, the expression "suitable incubation environment" means that optimal conditions for growth of the microorganism are provided, e.g., temperature in the range of 30 to 40° C., preferably 35 to 37° C., exchange of gases, in particular oxygen for aerobic microorganisms, etc. The suitable incubation environment may be provided by the incubation assembly and/or the carrier, such as a microfluidic chip, preferably the microfluidic chip as described in PL 425107. In the context of the present invention the expression "suitable measuring environment" means that the incubation assembly and the carrier allows for interrogating the one or more test assays comprised in the compartment(s) of the carrier and measuring the essentially monotonically correlated property/signal. In case the intensity of light (scattered light, fluorescence) is measured, the incubation assembly is preferably separated from light not emitted by the test assays, i.e. in other words the test assay is kept dark.

During incubation of the inoculated carrier in step d) of the method of the first aspect of the present invention, a signal derived from a chemical or physical property of the inoculated microorganism in the one or more test assays is measured at least n times for each test assay, with a constant or inconstant frequency $f$, wherein the signal represents an essentially monotonic function of the number of the microorganisms in the measured test assay, and corresponding n values $\{x_i\}$ are read out and recorded at corresponding recording times $\{t_i\}$, wherein i represents the index number of the measurement represented by an integer 1 to n, and wherein n represents a full integer of 13 or more measurements. In the context of the present application the expression "signal represents an essentially monotonic function of the number of microorganisms in the measured test assay" means that underlying measured chemical or physical property exhibiting the signal follows an essentially monotonic function in relation with the number of microorganisms in the measured test assay, whereby the high-frequency noise of the measuring instrument may deviate the signal from the monotonic function. The measurement step may be conducted by use of an interrogation and readout assembly comprising interrogation means and measuring means configured to interrogate and readout the one or more test assays during incubation of the one or more carriers. The signal derived from a chemical or physical property of the inoculated microorganism may preferably be selected from intensity of light, e.g., fluorescence or scattered light; optical density, absorbance, turbidity, light reflection or other optical properties; conductivity, capacitance or other electrical properties; partial pressures of gases involved in metabolism of the microorganism, viscosity or nutrient uptake, more preferably the intensity of light scattered while passing through the incubation compartment or the intensity of fluorescence emitted from a suitably excited microorganism sample, in particular in case the microorganism sample comprises resazurin, as actively metabolizing microorganisms produce resorufin as a reduction product of resazurin, which emits fluorescence after being suitably excited.

The frequency $f$ and, thus, the time interval between two consecutive measurements is preferably 1 mHz or more, more preferably $f$ is in the range of 10 mHz to 10 Hz, even more preferably in the range of 100 mHz to 1 Hz. In order to alleviate the underlying calculations, the frequency $f$ is preferably constant between all n recording times $\{t_1\}$.

According to the first aspect of the present invention, part or all of the n readout values $\{x_i\}$, but at least 13 or more readout values $\{x_i\}$ at corresponding recording times $\{t_i\}$ are used to estimate one or more slopes of linear trends $\alpha$ in data as a function of distribution of a difference from a subtraction of constituents of a pair of the readout values $\{x_i\}$ and $\{x_j\}$, where j>i, divided by the time interval $\delta t_{ij}$ between taking readouts indexed i and j. In other words, for at least 13 or more readout values $\{x_i\}$ a distribution of a difference from a subtraction of constituents of a pair of the readout values divided by the time interval between the readouts (related to the frequency $f$) can be prepared as follows:

As already set out above, from the set of n readouts $\{x_i\}$, a set of $$\frac{n(n-1)}{2}$$

normalized differences $\{\eta_{ij}\}$ of pairs of readouts $$\eta_{ij} = \frac{x_j - x_i}{\delta t_{ij}}$$

where j>i and $\delta t_{ij}$ is the time difference between taking readouts indexed i and j may be constructed. If the readouts are taken with constant frequency, then $\delta t_{ij}=\delta t(j-i)$, where $\delta t$ is the average time between consecutive readouts. The average difference $\bar\eta$ of all normalized differences $$\bar\eta = \frac{\sum_{j=2}^{n}\left(\sum_{i=1}^{j}\eta_{ij}\right)}{\frac{n(n-1)}{2}}$$

may be calculated. The average difference $\bar\eta$ is equal to the estimate $\hat\alpha$ of the slope of the series of readouts $\alpha$: $\bar\eta=\hat\alpha$. The inaccuracy $\sigma_\alpha$ of estimation of $\alpha$ is equal to $$\sigma_\alpha = \sqrt{\frac{4}{3} \frac{\pi\sigma}{\delta t} n^{-\frac{3}{2}}},$$

where σ is the standard deviation of the high frequency noise of the instrument.

If the readouts are recorded with a constant frequency, the time of recording the i-th readout $x_i$ is given by $t_i = T_0 + \delta t \cdot i$, where δt is the average time between the recording of two consecutive readouts, the above formulas may be mathematically derived as follows:

If the increase of recorded quantity is small, it can be closely approximated by a linear function. Therefore every readout can be approximated as a sum of Gaussian high frequency noise (i.e. the frequency of the noise $f_{noise}$ is higher than the frequency of taking readouts $$f_{readout} = \frac{1}{\delta t})$$

from me experimental setup, linear trend and a function describing the background from culture medium $f_{background}$.

Mathematically, if the variability of background from culture medium is negligible, i.e. $f_{background}(t) \approx C = const$, every readout can be described with the following sum: $x_i = N(0, \sigma) + \alpha \cdot (T_0 + \delta t \cdot i) + C$, where α is the slope of the linear trend in data, and therefore the measure of growth of microorganisms in culture, σ is the standard deviation of the high-frequency noise, δt is the time interval between consecutive readouts, $T_0$ is the starting time of the experiment, i is the number of readout and C is a constant describing background from culture medium. The symbol N(μ, σ) is used to denote the normal (or Gaussian or Gauss or Laplace-Gauss) distribution, where μ is the mean of the distribution, σ is the standard deviation of the distribution and $\sigma^2$ is the variance of the distribution. Therefore, every readout can be treated as a random variable with mean value $\alpha \cdot (T_0 + i \cdot \delta t) + C$ and standard deviation σ: $x_i \sim N(\alpha \cdot (T_0 + \delta t \cdot i) + C, \sigma)$.

The result of subtraction of one readout from another is also a random variable. Every readout can be seen as a sum of a true ("mean") value of signal and a deviation coming for example from a high-frequency noise from experimental setup. Therefore for result of such subtraction its mean is equal to the difference of means of readouts, and the standard deviation is equal to $\sqrt{2}\sigma$ (Bennett Eisenberg and Rosemary Sullivan, Why is the Sum of Independent Normal Random Variables Normal, Math. Magazine, 2008, Vol. 81, p 362-366). Hence the result of subtraction is given by the equation $x_j - x_i = N(0, \sigma) + \alpha \cdot j \cdot \delta t - N(0, \sigma) - \alpha \cdot i \delta t = N(0, \sqrt{2}\sigma) + \alpha \delta t(j-i)$, $(x_j - x_i) \sim N(\alpha \cdot \delta t(j-i), \sqrt{2}\sigma)$.

The result of a subtraction of two readouts indexed by i and j=i+k normalized by the time difference between the recording of the readouts $t_j - t_i = \delta t(j-i) = \delta t k$ is then given by $$\eta_k = \frac{N(0,\sigma) + \alpha \cdot (i+k) \cdot \delta t - N(0,\sigma) - \alpha \cdot i \cdot \delta t}{\delta t k} = N\left(0, \frac{\sqrt{2}\sigma}{\delta t k}\right) + \alpha$$

and is a random variable:

$$\eta_k \sim N\left(\alpha, \frac{\sigma\sqrt{2}}{\delta t k}\right).$$

The sum of results of all the subtractions $\eta_k$ from a set of n readouts, for fixed value of k, is given by the following equation:

$$\sum_{i=1}^{n-k} \eta_k = (n-k) \cdot \eta_k$$

and is also a random variable $$\sum_{i=1}^{n-k} \eta_k \sim N\left(\alpha \cdot (n-k), \frac{\sigma\sqrt{2(n-k)}}{\delta t k}\right)$$

The sum of results of all the subtractions $\eta_k$ from an entire set of n readouts for all values of k is given by the following equation:

$$\sum_{k=1}^{n-1}\left(\sum_{i=1}^{n-k} \eta_k\right) = \sum_{k=1}^{n-1} ((n-k) \cdot \eta_k)$$

and is a random variable $$\sum_{k=1}^{n-1}\left(\sum_{i=1}^{n-k} \eta_k\right) \sim N\left(\alpha \cdot \frac{n(n-1)}{2}, \frac{\sigma}{\delta t}\sqrt{2\sum_{k=1}^{n-1}\frac{n-k}{k^2}}\right).$$

Therefore, the average normalized subtraction of any two from a set of n readouts (which makes $$\frac{n(n-1)}{2}$$

subtractions) has the following distribution:

$$p(\eta) = \frac{2}{n(n-1)} N\left(\alpha \frac{n(n-1)}{2}, \frac{\sigma}{\delta t}\sqrt{2\sum_{k=1}^{n-1}\left(\frac{n-k}{k^2}\right)}\right) =$$

$$N\left(\alpha, \frac{2\sqrt{2}}{n(n-1)} \frac{\sigma}{\delta t}\sqrt{\sum_{k=1}^{n-1}\left(\frac{n-k}{k^2}\right)}\right).$$

The series $$\sum_{k=1}^{n-1}\left(\frac{n-k}{k^2}\right),$$

can be rewritten as a sum of two series:

$$n\sum_{k=1}^{n-1}\frac{1}{k^2} - \sum_{k=1}^{n-1}\frac{1}{k}$$

and its upper bound can be closely approximated by $$\frac{n\pi^2}{6}$$

for large n (for n=13, the result of the approximation is $$\sqrt{\frac{n\pi^2}{6}} \approx 1.11 \cdot \sqrt{\sum_{k=1}^{n-1}\left(\frac{n-k}{k^2}\right)},$$

for n>15 the difference is smaller than 10%, and for n>33, the difference is smaller than 5%) according to Riemann's hypothesis (Basel problem). Also, for a large n, the upper bound of the term $$\frac{1}{n(n-1)}$$

can be approximated by $$\frac{1}{n^2}.$$

Finally, the distribution of the average normalized subtraction is equal to $$p(\eta) \sim N\left(\alpha, \sqrt{\frac{4}{3}\frac{\pi\sigma}{\delta t}n^{-\frac{3}{2}}}\right).$$

Therefore, calculating the average normalized subtraction provides the estimate of the linear trend α with standard deviation of $$\sqrt{\frac{4}{3}\frac{\pi\sigma}{\delta t}}n^{-\frac{3}{2}}.$$

According to the first aspect of the present invention the qualitative or quantitative susceptibility of the inoculated microorganism against the single antimicrobial agent or the combination of antimicrobial agents is determined as a function of one or more slopes of linear trends α.

The qualitative or quantitative susceptibility of the inoculated microorganism is based on the finding, whether the growth of the inoculated microorganism is inhibited or not. Accordingly, the growth rate μ of the inoculated microorganism in the test assay y may be calculated using a calibration function $f(y)$: $\mu=(f'(y))^{-1}\cdot\alpha$.

Preferably, the value of Minimum Inhibitory Concentration can be determined as:
i. The crossing of the line tangent to the growth rate vs. antibiotic concentration dependence at the point of highest slope (Chorianopoulos, N. G., Lambert, R. J. W., Skandamis, P. N., Evergetis, E. T., Haroutounian, S. A. and Nychas, G.-J. E. (2006), A newly developed assay to study the minimum inhibitory concentration of *Satureja spinosa* essential oil. Journal of Applied Microbiology, 100: 778-786. doi:10.1111/j.1365-2672.2006.02827.x; Lambert, R. J. W. and Pearson, J. (2000), Susceptibility testing: accurate and reproducible minimum inhibitory concentration (MIC) and non-inhibitory concentration (NIC) values. Journal of Applied Microbiology, 88: 784-790. doi:10.1046/j.1365-2672.2000.01017.x; Lambert, R. J. W. and Lambert, R. (2003), A model for the efficacy of combined inhibitors. Journal of Applied Microbiology, 95: 734-743. doi:10.1046/j.1365-2672.2003.02039.x).
ii. The lowest examined concentration of antibiotic at which the growth rate (linear trend in data) is lower than a given threshold.

The inaccuracy $\sigma_\mu$ of estimation of growth rate μ is equal to $\sigma_\mu=|f'(y)|^{-1}\cdot\sigma_\alpha=|f'(y)|^{-1}\cdot$ $$\sqrt{\frac{4}{3}\frac{\pi\sigma}{\delta t}}n^{-\frac{3}{2}},$$

where σ is the standard deviation of the high frequency noise of the instrument.

This means that the precision of the qualitative or quantitative susceptibility determination i.e. standard deviation $\sigma_\alpha$ of an estimation of the linear trend α depends only on the number of readouts used for the distribution of difference from the subtraction and the standard deviation of the high frequency noise from the measuring means σ. Moreover it is proportional to $$n^{-\frac{3}{2}} = \left(n^{-\frac{1}{2}}\right)^3,$$

which means that the precision of the determination of the qualitative or quantitative susceptibility of the sample of inoculated microorganism increases faster with growing number of readouts than in the usual AST methods according to the prior art, e.g. least square method, where a scaling factor is $$n^{-\frac{1}{2}}.$$

The aspects of present invention also apply to situations where readouts are not recorded with a constant frequency. One example of taking readouts with inconstant frequency is the case where the readouts are distributed between a number M of sets. The set is defined as a subset of the total of readouts that are consecutive, and the values of time intervals between taking consecutive readouts belonging to the same set have the same distribution. Each set comprises a number $M_i$ of readouts, where $$\sum_{i=1}^{M} m_i = n$$

it the total number of readouts in all the sets. The average time interval between taking the consecutive readouts belonging to the i-th set is given as $\delta t_i$. The time of taking the first readout of the i-th set is given as $T_i$. Therefore, the time $t_{ij}$ of taking the j-th readout from i-th set is given by $t_{ij}=T_0+T_i+\delta t_i\cdot j$.

In this case, the formulas for the estimate a of the slope of the series of readouts α: $\tilde{\eta}=\tilde{\alpha}$ and the inaccuracy $\sigma_\alpha$ may be mathematically derived as follows:

If the increase of recorded quantity is small, it can be closely approximated by a linear function. Therefore every readout can be approximated as a sum of Gaussian high frequency noise (i.e. the frequency of the noise $f_{noise}$ is higher than the frequency of taking readouts belonging to any of the sets $$f_{readout} = \frac{1}{\delta t_i}$$

for i∈ <1; M>) from the experimental setup, linear trend and a function describing the background from culture medium $f_{background}$.

Mathematically, if the variability of background from culture medium is negligible, i.e. $f_{background}(t)\approx$const, every readout can be described with the following sum: $x_{ij}=N(0,\sigma)+\alpha\cdot(T_0+T_i+\delta t_i\cdot j)+C$, where α is the slope of the linear trend in data, and therefore the measure of growth of microorganisms in culture, a is the standard deviation of the high-frequency noise, i is the index of set to which the readout belongs, j is the number of readout within the set (therefore $x_{ij}$ represents the j-th readout from i-th set), $\delta t_i$ is the time interval between consecutive readouts belonging to the i-th set, $T_0$ is the starting time of the experiment, $T_0$ is the starting time of taking readouts belonging to the i-th set and C is a constant describing background from culture medium. The symbol N ($\mu$,$\sigma$) is used to denote the normal (or Gaussian or Gauss or Laplace-Gauss) distribution, where $\mu$ is the mean of the distribution, $\alpha$ is the standard deviation of the distribution and $\sigma^2$ is the variance of the distribution. Therefore, every readout can be treated as a random variable with mean value $\alpha \cdot (T_0+T_i+\delta t_i \cdot j)+C$ and standard deviation $\sigma$: $x_{ij} \sim N(\alpha \cdot (T_0+T_i+\delta t_i \cdot j)+C, \sigma)$.

The result of subtraction of one readout from another is also a random variable. Every readout can be seen as a sum of a true ("mean") value of signal and a deviation coming for example from a high frequency noise from experimental setup. Therefore for result of such subtraction its mean is equal to the difference of means of readouts, and the standard deviation is equal to $\sqrt{2}\sigma$ (Bennett Eisenberg and Rosemary Sullivan, Why is the Sum of Independent Normal Random Variables Normal, Math. Magazine, 2008, Vol. 81, p 362-366). Hence the result of subtraction is given by the equation $x_{ij}-x_{i'j'}=N(0, \sigma)+\alpha \cdot (T_0+T_i+\delta t_i \cdot j)+C-N(0, \sigma)-\alpha \cdot (T_0+T_i+\delta t_i \cdot j')-C=N(0,\sqrt{2}\sigma)+\alpha(T_i-T_i+\delta t_i \cdot j-\delta t_i \cdot j')$, $(x_{ij}-x_{i'j'}) \sim N(\alpha T_i-T_i+\delta t_i \cdot j-\delta t_i \cdot j'), \sqrt{2}\sigma)$.

If two readouts belong to the same set, indexed i, i.e. i'=i, the result of a subtraction of the two readouts indexed by j and j'=j+k normalized by the time difference between the recording of the readouts $t_{ij'}-t_{ij}=\delta t_i(j'-j)=\delta t_i k$ is then given by $$\eta_{ij'ij} = \eta_{i(j+k)ij} =$$

$$\eta_{ik} = \frac{N(0, \sigma)+\alpha \cdot (j+k)\cdot \delta t_i - N(0,\sigma) - \alpha \cdot j \cdot \delta t_i}{\delta t_i k} = N\left(0, \frac{\sqrt{2}\sigma}{\delta t_i k}\right) + \alpha$$

and is a random variable:

$$\eta_{ik} \sim N\left(\alpha, \frac{\sigma\sqrt{2}}{\delta t_i k}\right).$$

The sum of results of all the subtractions $\eta_{ik}$ from a $m_i$ readouts belonging to the i-th set, for fixed value of k, is given by the following equation:

$$\sum_{l=1}^{m_i-k} \eta_{ik} = (m_i-k) \cdot \eta_{ik}$$

and is also a random variable $$\sum_{l=1}^{m_i-k} \eta_{ik} \sim N\left(\alpha \cdot (m_i-k), \frac{\sigma\sqrt{2(m_i-k)}}{\delta t_i k}\right)$$

The sum of results of all the subtractions $\eta_{ik}$ from all $m_i$ readouts from the i-th set for all values of k is given by the following equation:

$$\sum_{k=1}^{m_i-1}\left(\sum_{l=1}^{m_i-k} \eta_{ik}\right) = \sum_{k=1}^{m_i-1}((m_i-k) \cdot$$

$\eta_{ik})$ and is a random variable $$\sum_{k=1}^{m_i-1}\left(\sum_{l=1}^{m_i-k} \eta_{ik}\right) \sim$$

-continued $$N\left(\alpha \cdot \frac{m_i(m_i-1)}{2}, \frac{\sigma}{\delta t_i}\sqrt{2\sum_{k=1}^{m_i-1}\frac{m_i-k}{k^2}}\right) \approx N\left(\alpha \cdot \frac{m_i(m_i-1)}{2}, \frac{\sigma\pi}{\delta t_i}\sqrt{\frac{m_i}{3}}\right).$$

Therefore, the sum of all the subtractions $\eta_{ik}$ for all the pairs of readouts belonging to same library is equal $$\sum_{i=1}^{M}\sum_{k=1}^{m_i-1}\left(\sum_{l=1}^{m_i-k}\eta_{ik}\right) = \sum_{i=1}^{M}\sum_{k=1}^{m_i-1}((m_i-k)\cdot \eta_{ik})$$

and is a random variable $$\sum_{i=1}^{M}\sum_{k=1}^{m_i-1}\left(\sum_{l=1}^{m_i-k}\eta_{ik}\right) \sim$$

$$N\left(\sum_{i=1}^{M}\left(\alpha \cdot \frac{m_i(m_i-1)}{2}\right), \sqrt{2\sum_{i=1}^{M}\sum_{k=1}^{m_i-1}\left[\left(\frac{\sigma}{\delta t_i}\right)^2\left(\frac{m_i-k}{k^2}\right)\right]}\right).$$

If the number $m_i$ of readouts belonging to the i-th library is constant for any i, i.e. $\forall_{i \in <1;M>} m_i = m$, and the time interval $\delta t_i$ between taking the consecutive readouts belonging to the i-th library is constant for any i, i.e. $\forall_{i \in <1;M>} \delta t_i = \delta t$, this distribution can be simplified to:

$$\sum_{i=1}^{M}\sum_{k=1}^{m_i-1}\left(\sum_{l=1}^{m_i-k}\eta_{ik}\right) \sim$$

$$N\left(\sum_{i=1}^{M}\left(\alpha \cdot \frac{m(m-1)}{2}\right), \sqrt{2\sum_{i=1}^{M}\sum_{k=1}^{m-1}\left[\left(\frac{\sigma}{\delta t}\right)^2\left(\frac{m-k}{k^2}\right)\right]}\right) =$$

$$N\left(\alpha M \cdot \frac{m(m-1)}{2}, \frac{\sigma\pi}{\delta t}\sqrt{\frac{M \cdot m}{3}}\right) = N\left(\alpha\frac{n(m-1)}{2}, \frac{\sigma\pi}{\delta t}\sqrt{\frac{n}{3}}\right).$$

If two readouts belong to different sets, indexed i and i', the result of a subtraction of the two readouts indexed by j (i.e. j-th readout in the i-th set) and j' (i.e. j'-th readout in the i'-th set) normalized by the time difference between the recording of the readouts $t_{i'j'}-t_{ij}=T_{i'}-T_i+\delta t_{i'} \cdot j' - \delta t_i \cdot j = \Delta T_{ii'} + \delta t_{i'} \cdot j' - \delta t_i \cdot j$ is then given by $$\eta_{i'j'ij} = \frac{N(0,\sigma)+\alpha\cdot(T_{i'}+\delta t_{i'}\cdot j')-N(0,\sigma)-\alpha\cdot(T_i+\delta t_i \cdot j)}{\Delta T_{ii'}+\delta t_{i'}\cdot j' - \delta t_i \cdot j} =$$

$$N\left(0, \frac{\sqrt{2}\sigma}{\Delta T_{ii'}+\delta t_{i'}\cdot j' - \delta t_i \cdot j}\right) + \alpha$$

and is a random variable:

$$\eta_{i'j'ij} \sim N\left(\alpha, \frac{\sigma\sqrt{2}}{\Delta T_{ii'}+\delta t_{i'},\cdot j' - \delta t_i \cdot j}\right).$$

The sum $$\sum_{j=1}^{m_i}\eta_{i'j'ij}$$

of results of all the subtractions $\eta_{ij'ij}$ of all $m_i$ readouts belonging to the i-th set from the j'-th readout belonging to the i'-th set, is also a random variable $$\sum_{j'=1}^{m_{i'}} \eta_{i'j'ij} \sim N\left(\alpha \cdot m_i, \sigma\sqrt{2}\sqrt{\sum_{j=1}^{m_i}\left(\frac{1}{\Delta T_{ii'} + \delta t_{i'} \cdot j' - \delta t_i \cdot j}\right)^2}\right).$$

The sum $$\sum_{j'=1}^{m_{i'}} \sum_{j=1}^{m_i} \eta_{i'j'ij}$$

of results of all the subtractions $\eta_{i'j'ij}$ from all $m_i$ readouts belonging to the i-th set from all $m_{i'}$ readouts belonging to the i'-th set from the i-th set, is also a random variable $$\sum_{j'=1}^{m_{i'}} \sum_{j=1}^{m_i} \eta_{i'j'ij} \sim$$
$$N\left(\alpha \cdot m_i \cdot m_{i'}, \sigma\sqrt{2}\sqrt{\sum_{j'=1}^{m_{i'}}\sum_{j=1}^{m_i}\left(\frac{1}{\Delta T_{ii'} + \delta t_{i'} \cdot j' - \delta t_i \cdot j}\right)^2}\right).$$

In some practical applications, it is particularly advantageous if time intervals $\Delta T_{ii'}=T_{i'}-T_i$ between starting collecting readouts from consecutive sets are larger than time $\delta t_i \cdot m_i$ of taking all the readouts belonging to a single set, i.e. $\Delta T_{ii'} >> \delta t_i \cdot m_i$.

In this case, the summation $\Delta T_{ii'}+\delta t_{i'} \cdot j'-\delta t_i \cdot j$ can be closely approximated with $\Delta T_{ii'}$, therefore the sum $$\sum_{j'=1}^{m_{i'}} \sum_{j=1}^{m_i} \eta_{i'j'ij}$$

of results of all the subtractions $\eta_{i'j'ij}$ from all $m_i$ readouts belonging to the i-th set from all $m_{i'}$ readouts belonging to the i'-th set from the i-th set, can be described as:

$$\sum_{j'=1}^{m_{i'}} \sum_{j=1}^{m_i} \eta_{i'j'ij} \sim N\left(\alpha \cdot m_i \cdot m_{i'}, \sigma\sqrt{2}\sqrt{\sum_{j'=1}^{m_{i'}}\sum_{j=1}^{m_i}\frac{1}{\Delta T_{ii'}^2}}\right).$$

If time intervals $\Delta T$ between consecutive sets are constant, i.e. or any $\Delta T_{i(i+1)}=\Delta T$, the summation is equal:

$$\sum_{j'=1}^{m_{i'}} \sum_{j=1}^{m_i} \eta_{i'j'ij} \sim N\left(\alpha \cdot m_i \cdot m_{i'}, \sigma\sqrt{2}\sqrt{\sum_{j'=1}^{m_{i'}}\sum_{j=1}^{m_i}\frac{1}{(\Delta T(i'-i))^2}}\right) =$$
$$N\left(\alpha \cdot m_i \cdot m_{i'}, \frac{\sigma\sqrt{2}}{\Delta T(i'-i)}\sqrt{m_i \cdot m_{i'}}\right).$$

The above summation covers all the normalized subtractions of readouts belonging to one set indexed i from readouts belonging to set indexed i', where i≠i'. Therefore, the sum of all subtractions of readouts from one set from readouts from another set for all pairs of different sets is given by:

$$\sum_{i'=2}^{M} \sum_{i=1}^{i'-1} \sum_{j'=1}^{m_{i'}} \sum_{j=1}^{m_i} \eta_{i'j'ij}.$$

Here it is assumed that the higher the index i of the set is, the later readouts it comprises (i.e. $\forall_{i'>i} T_{i'}>T_i$).

The sum of all subtractions of readouts from one set from readouts from another set for all pairs of different sets is a random variable given by the following distribution:

$$\sum_{i'=2}^{M} \sum_{i=1}^{i'-1} \sum_{j'=1}^{m_{i'}} \sum_{j=1}^{m_i} \eta_{i'j'ij} \sim$$
$$N\left(\sum_{i'=2}^{M} \sum_{i=1}^{i'-1}(\alpha \cdot m_i \cdot m_{i'}), \frac{\sigma\sqrt{2}}{\Delta T}\sqrt{\sum_{i'=2}^{M}\sum_{i=1}^{i'-1}\left(\frac{m_i \cdot m_{i'}}{(i'-i)^2}\right)}\right).$$

If the number $m_i$ of readouts belonging to the i-th library is constant for any i, i.e. $\forall_{i \in <1;M>} m_i = m$, and the difference of indices i' and i is replaced by $l=i'-i$, this distribution can be simplified to $$\sum_{i'=2}^{M} \sum_{i=1}^{i'-1} \sum_{j'=1}^{m} \sum_{j=1}^{m} \eta_{i'j'ij} \sim$$
$$N\left(\frac{M(M-1)}{2} \cdot \alpha \cdot m^2, \frac{\sigma m\sqrt{2}}{\Delta T}\sqrt{\sum_{l=1}^{M-1}\left(\frac{n-l}{l^2}\right)}\right).$$

As it was shown earlier, this can be further simplified to $$\sum_{i'=2}^{M} \sum_{i=1}^{i'-1} \sum_{j'=1}^{m} \sum_{j=1}^{m} \eta_{i'j'ij} \sim$$
$$N\left(\frac{M(M-1)}{2} \cdot \alpha \cdot m^2, \frac{\sigma m\sqrt{2}}{\Delta T}\sqrt{\frac{\pi^2 M}{6}}\right) =$$
$$N\left(\frac{M(M-1)}{2} \cdot \alpha \cdot m^2, \frac{\sigma m\pi}{\Delta T}\sqrt{\frac{M}{3}}\right).$$

Having calculated the sum of all subtractions for all the pairs of readouts belonging to different libraries, and the sum of all subtractions for all the pairs of readouts belonging to the same library, it is possible to calculate the sum of the normalized subtractions of all $n(n-1)/2$ pairs of readouts from the total of n readouts.

The sum of all the subtractions for all the pairs of readouts is equal to:

$$\sum_{i=1}^{M} \sum_{j=1}^{m_i-1} \sum_{i'=1}^{M} \sum_{j'=1}^{m_{i'}-1} \left(\eta_{i'j'ij}\right)_{\{ij \neq i'j' \wedge t_{i'j'} > t_{ij}\}} =$$
$$\sum_{i=1}^{M} \sum_{k=1}^{m_i-1}\left(\sum_{l=1}^{m_i-k} \eta_{ik}\right) + \sum_{i'=2}^{M} \sum_{i=1}^{i'-1} \sum_{j'=1}^{m_{i'}} \sum_{j=1}^{m_i} \eta_{i'j'ij}.$$

It is also a sum of random variables, therefore it is also a random variable:

$$\sum_{i=1}^{M} \sum_{j=1}^{m_i-1} \sum_{i'=1}^{M} \sum_{j'=1}^{m_{i'}-1}\left(\eta_{iji'j'}\right)_{\{ij \neq i'j' \wedge t_{i'j'} > t_{ij}\}} \sim$$
$$N\left(\alpha\frac{n(m-1)}{2}, \frac{\sigma\pi}{\delta t}\sqrt{\frac{n}{3}}\right) + N\left(\frac{M(M-1)}{2} \cdot \alpha \cdot m^2, \frac{\sigma m\pi}{\Delta T}\sqrt{\frac{M}{3}}\right) =$$
$$N\left(\alpha\left(\frac{n(m-1)}{2} + \frac{M(M-1)}{2} \cdot m^2\right), \sqrt{\left(\frac{\sigma\pi}{\delta t}\sqrt{\frac{n}{3}}\right)^2 + \left(\frac{\sigma m\pi}{\Delta T}\sqrt{\frac{M}{3}}\right)^2}\right) =$$
$$N\left(a\frac{n(n-1)}{2}, \frac{\sigma\pi}{\sqrt{3}}\sqrt{\frac{n}{\delta t^2} + \frac{nm}{\Delta T^2}}\right)$$

Therefore, the average normalized subtraction of any two from a of n readouts (which makes $$\frac{n(n-1)}{2}$$

subtractions) has the following distribution:

$$p(\eta) = \frac{2}{n(n-1)} N\left(a \frac{n(n-1)}{2}, \frac{\sigma\pi}{\sqrt{3}} \sqrt{\frac{n}{\delta t^2} + \frac{nm}{\Delta T^2}}\right) =$$

$$N\left(\alpha, \sqrt{\frac{4}{3} \frac{\pi\sigma}{n(n-1)}} \sqrt{\frac{n}{\delta t^2} + \frac{nm}{\Delta T^2}}\right).$$

Therefore, calculating the average normalized subtraction provides the estimate of the linear trend α with standard deviation of $$\sqrt{\frac{4}{3} \frac{\pi\sigma}{n(n-1)}} \sqrt{\frac{n}{\delta t^2} + \frac{nm}{\Delta T^2}}.$$

The inaccuracy $\sigma_\mu$ of estimation of growth rate μ is equal to $$\sigma_\mu = |f'(y)|^{-1} \cdot \sigma_\alpha = |f'(y)|^{-1} \cdot \sqrt{\frac{4}{3} \frac{\pi\sigma}{n(n-1)}} \sqrt{\frac{n}{\delta t^2} + \frac{nm}{\Delta T^2}},$$

where σ is the standard deviation of the high frequency noise of the instrument.

This means that the precision of the qualitative or quantitative susceptibility determination (i.e. standard deviation $\sigma_\alpha$ of an estimation of the linear trends α) depends only on the number and distribution of readouts used for the calculation of the distribution of subtraction and the standard deviation of the high frequency noise from the measuring means a.

Another example of taking readouts with inconstant frequency is the case where the time of taking every readout is determined by an arbitral injective function of the number of readout. Therefore, the time of taking the i-th readout is given by $t_i = T_0 + f(i)$.

In this case, the formulas for the estimate $\hat{\alpha}$ of the slope of the series of readouts α: $\overline{\eta} = \hat{\alpha}$ and the inaccuracy $\sigma_\alpha$ may be mathematically derived as follows:

If the increase of recorded quantity is small, it can be closely approximated by a linear function. Therefore every readout can be approximated as a sum of Gaussian high frequency noise (i.e. the frequency of the noise $f_{noise}$ is higher than the highest frequency of taking readouts $$f_{readout}^{max} = \frac{1}{t_{i+1} - t_i}$$

for i∈ <1; n>) from the experimental setup, linear trend and a function describing the background from culture medium $f_{background}$.

Mathematically, if the variability of background from culture medium is negligible, i.e. $f_{background}(t) \approx C = const$, every readout can be described with the following sum: $x_i = N(0, \sigma) + \alpha \cdot (T_0 + f(i)) + C$, where α is the slope of the linear trend in data, and therefore the measure of growth of microorganisms in culture, α is the standard deviation of the high-frequency noise, i is the index of the readout, $T_0$ is the starting time of the experiment, $f(i)$ is the starting time of taking the readout and C is a constant describing background from culture medium. The symbol N(μ, σ) is used to denote the normal (or Gaussian or Gauss or Laplace-Gauss) distribution, where μ is the mean of the distribution, σ is the standard deviation of the distribution and $\sigma^2$ is the variance of the distribution. Therefore, every readout can be treated as a random variable with mean value $\alpha \cdot (T_0 + f(i)) + C$ and standard deviation σ: $x_i \sim N(\alpha \cdot (T_0 + f(i)) + C, \sigma)$.

The result of subtraction of one readout from another is also a random variable. Every readout can be seen as a sum of a true ("mean") value of signal and a deviation coming for example from a high frequency noise from experimental setup. Therefore for result of such subtraction its mean is equal to the difference of means of readouts, and the standard deviation is equal to $\sqrt{2}\sigma$ (Bennett Eisenberg and Rosemary Sullivan, Why is the Sum of Independent Normal Random Variables Normal, Math. Magazine, 2008, Vol. 81, p 362-366). Hence the result of subtraction is given by the equation $x_j - x_i = N(0, \sigma) + \alpha \cdot f(j) - N(0, \sigma) - \alpha \cdot f(i) = N(0, \sqrt{2}\sigma) + \alpha(f(j) - f(i))$, $(x_j - x_i) \sim N(\alpha \cdot (f(j) - f(i)), \sqrt{2}\sigma)$.

The result of a subtraction of two readouts indexed by i and j normalized by the time difference between the recording of the readouts $t_j - t_i = f(j) - f(i)$ is then given by $$\eta_{ij} = \frac{N(0, \sigma) + \alpha \cdot f(j) - N(0, \sigma) - \alpha \cdot f(i)}{f(j) - f(i)} = N\left(0, \frac{\sqrt{2}\sigma}{f(j) - f(i)}\right) + \alpha$$

and is a random variable:

$$\eta_{ij} \sim N\left(\alpha, \frac{\sigma\sqrt{2}}{f(j) - f(i)}\right).$$

The sum of results of all the subtractions $\eta_{ij}$ from an entire set of n readouts for all values of i and j, while j≠i, is given by the following equation:

$$\sum_{j=2}^{n} \sum_{i=1}^{j} \eta_{ij} = \sum_{j=2}^{n} \sum_{i=1}^{j} \left(\frac{N(0, \sigma) + \alpha \cdot f(j) - N(0, \sigma) - \alpha \cdot f(i)}{f(j) - f(i)}\right)$$

and is a random variable $$\sum_{j=2}^{n} \sum_{i=1}^{j} \eta_{ij} \sim N\left(\alpha \cdot \frac{n(n-1)}{2}, \sqrt{2}\sigma \sqrt{\sum_{j=2}^{n} \sum_{i=1}^{j} \frac{1}{(f(j) - f(i))^2}}\right).$$

Therefore, the average normalized subtraction of any two from a set of n readouts (which makes $$\frac{n(n-1)}{2}$$

subtractions) has me following distribution:

$$p(\eta) =$$

$$\frac{2}{n(n-1)} N\left(\alpha \cdot \frac{n(n-1)}{2}, \sqrt{2}\sigma \sqrt{\sum_{j=2}^{n} \sum_{i=1}^{j} \frac{1}{(f(j) - f(i))^2}}\right) =$$

$$N\left(\alpha, \frac{2\sqrt{2}\sigma}{n(n-1)} \sqrt{\sum_{j=2}^{n} \sum_{i=1}^{j} \frac{1}{(f(j) - f(i))}}\right).$$

Finally, the distribution of the average normalized difference from a subtraction is equal to $$p(\eta) \sim N\left(\alpha, \frac{2\sqrt{2}\,\sigma}{n(n-1)}\sqrt{\sum_{j=2}^{n}\sum_{i=1}^{j}\frac{1}{(f(j)-f(i))^2}}\right).$$

Therefore, the standard deviation of the estimate of the linear trend α provided from the calculation of the average normalized difference from the subtraction depends on the arbitral (user-defined) function $f(i)$ of taking the i-th readout and equals $$\frac{2\sqrt{2}\,\sigma}{n(n-1)}\sqrt{\sum_{j=2}^{n}\sum_{i=1}^{j}\frac{1}{(f(j)-f(i))^2}}.$$

If the function $f(i)$ is also a random variable, e.g. $f(i)=T_0+\delta t \cdot i+N(0, \sigma_t)$, i.e. the time interval $\Delta f=f(i+1)-f(i)$ between taking consecutive readouts is a random variable with constant expected (average) value δt and standard deviation $\sigma_t$: $\Delta f \sim N(\delta t, \sigma_t)$, the result of a subtraction of two readouts indexed by i and j normalized by the time difference between the recording of the readouts $t_j-t_i=f(j)-f(i)=\Delta f(j-i) \sim N(\delta t \cdot (j-i), \sigma_t\sqrt{2})$ (Bennett Eisenberg and Rosemary Sullivan, Why is the Sum of Independent Normal Random Variables Normal, Math. Magazine, 2008, Vol. 81, p 362-366) is then given by $$\eta_{ij} = \frac{(0, \sigma) + \alpha \cdot (T_0 + \Delta f \cdot j) - N(0, \sigma) - \alpha \cdot (T_0 + \Delta f \cdot i)}{\Delta f \cdot j - \Delta f \cdot i} =$$
$$\frac{N(0, \sigma\sqrt{2}) + \alpha \cdot \Delta f \cdot (j-i)}{\Delta f \cdot (j-i)} =$$
$$\frac{N(0, \sigma\sqrt{2}) + N(\alpha \cdot \delta t \cdot (j-i), \alpha \cdot \sigma_t \sqrt{2})}{\delta t \cdot (j-i)} =$$
$$\frac{N(\alpha \cdot \delta t \cdot (j-i), \sqrt{2(\sigma^2 + \alpha^2 \cdot \sigma_t^2)})}{\delta t \cdot (j-i)} = N\left(\alpha, \frac{\sqrt{2(\sigma^2 + \alpha^2 \cdot \sigma_t^2)}}{\delta t \cdot (j-i)}\right).$$

In the practical applications of the presented invention, the increase of signal during the total time of the experiment is comparable to the value σ of the standard deviation of the high-frequency noise from the measuring means. Also, in practical applications, the relative spread $$\frac{\sigma_t}{\delta t}$$

of the values time intervals between taking consecutive readouts is less than 100%. Therefore, the average value of the product $\alpha \sigma_t$ is n times lower than the value σ of the standard deviation of the high-frequency noise from the measuring means, where n is the number of readouts. Since the preferred number n of readouts is bigger than 12, the increase of the standard deviation of the result of a subtraction of two readouts is less than 1%.

Hence, the distribution of the average normalized difference from a subtraction of two readouts in case of random time interval between taking consecutive readouts can be closely approximated by the distribution of average normalized difference from the subtraction of two readouts in case of constant time interval, i.e. can be approximated by $$p(\eta) \sim N\left(\alpha, \sqrt{\frac{4}{3}\frac{\pi\sigma}{\delta t}n^{-\frac{3}{2}}}\right).$$

Therefore, calculating the average normalized difference from the subtraction provides the estimate of the linear trend α with standard deviation of $$\sqrt{\frac{4}{3}\frac{\pi\sigma}{\delta t}}n^{-\frac{3}{2}}.$$

The inaccuracy $\sigma_\mu$ of estimation of growth rate μ is equal to $\sigma_{82}=|f'(y)|^{-1} \cdot \sigma_\alpha=|f'(y)|^{-1}$.

$$\sqrt{\frac{4}{3}\frac{\pi\sigma}{\delta t}}n^{-\frac{3}{2}},$$

where σ is the standard deviation of the high frequency noise of the instrument.

This means that the precision of the qualitative or quantitative susceptibility determination (i.e. standard deviation $\sigma_\alpha$ of an estimation of the linear trend α) depends only on the number of readouts used for the distribution of difference from the subtraction and the standard deviation of the high frequency noise from the measuring means σ. Moreover it is proportional to $$n^{-\frac{3}{2}} = \left(n^{-\frac{1}{2}}\right)^3,$$

which means that the precision of the determination of the qualitative or quantitative susceptibility of the sample of inoculated microorganism increases faster with growing number of readouts than in the usual AST methods according to the prior art, e.g. least square method, where a scaling factor is $$n^{-\frac{1}{2}}.$$

The aspects of the present invention are in particular advantageous, as the inventive method and system facilitate to take at least part of the n measurements in a phase of microorganism growth, wherein the changes of measured signal value due to the microbial population growth are smaller than the changes of the signal value due to the high-frequency noise of the measuring means. Accordingly, the inventive method allows determination of the qualitative and quantitative susceptibility of microorganisms earlier than the standard prior art antimicrobial susceptibility tests. In particular the inventive method is preferred, wherein the measurements in step e) are taken in a phase of microorganism growth, wherein the increase in measured signal due to the microorganism growth is equal or less than 3-fold of the high-frequency noise of the measuring means, preferably equal or less than 2-fold of the high-frequency noise of the measuring means, more preferably equal or less than 1-fold of the high-frequency noise of the measuring means. Accordingly, the measurements may be taken during the whole incubation time as set out in the respective guidelines of EUCAST and CLSI, but according to preferred embodiments, the measurements can also be taken during less than the usual incubation time (for bacteria approximately 16 hours), namely the time of microorganism growth, wherein the increase in measured signal due to the microorganism growth is equal or less than 3-fold of the high-frequency noise of the measuring means, preferably equal or less than 2-fold of the high-frequency noise of the measuring means, more preferably equal or less than 1-fold of the high frequency noise of the measuring means.

According to the first aspect of the present invention, one or more slopes of linear trends α can preferably be estimated with a predetermined standard deviation $\sigma_\alpha$ by calculating the minimum number of readouts n as a function of a standard deviation σ of a high frequency noise of the measuring means and time interval δt between consecutive readouts.

In order to calculate the minimum number of readouts n, the standard deviation σ of the high frequency noise of the instrument and time interval δt between the consecutive readouts have to be known.

The calculation may start with the determination of the maximum allowable standard deviation $\sigma_\alpha$ of the estimate of the linear trend α provided by the analysis of the set of n readouts.

The value $\sigma_\alpha$ determines the inaccuracy of assessment of the one or more linear trends α, which is equal to the first derivative of readouts in respect to time dx/dt.

This determines indirectly the behavior of the physical or biological system. The relationship between the value x of readout (i.e. physical or chemical property of the sample such as light scattering/transmitting properties, absorbance, optical density, turbidity, viscosity, pressure, electrical quantities etc.) and the actual parameter of interest y (i.e. density of bacterial culture, concentration of analyte, number of microorganisms etc.) is given by the bijective calibration function $f$: $x=f(y)$. The parameter α, being the slope of the series of readouts, is equal to dx/dt, therefore it is also related to the first derivative of the parameter of interest in respect to time dy/dt (i.e. growth rate μ) with the following equation:

$$\frac{dx}{dt} = \frac{dx}{dy} \cdot \frac{dy}{dt},$$

where $$\frac{dx}{dt} = \alpha, \frac{dx}{dy} = f'(y), \text{ and } \frac{dy}{dt} = \mu.$$

It can be rewritten as: $\alpha = f'(y) \cdot \mu$. If $f(y)$ is a linear function, the relation between α and μ reduces to simple linear scaling.

The maximum allowable standard deviation $\sigma_\alpha$ can be calculated from the requested maximum allowable standard deviation $\sigma_\mu$ of the estimate of growth rate μ: $\sigma_\alpha = |f'(y)| \cdot \sigma_\mu$.

Knowing the calibration function $x=f(y)$ and having determined the maximum allowable standard deviation $\sigma_\mu$ and $\sigma_\alpha$, one can transform a formula for a standard deviation of α derived in the previous subsection and calculate the minimum value of n using the following equation:

$$n = \sqrt[3]{\frac{4}{3}\left(\frac{\pi\sigma}{\delta t \sigma_\alpha}\right)^{\frac{2}{3}}} = \sqrt[3]{\frac{4}{3}\left(\frac{\pi\sigma}{\delta t |f'(y)| \sigma_\mu}\right)^{\frac{2}{3}}}$$

where n>12, σ>0, $\sigma_\alpha$>0, $\sigma_\mu$>0, and $f'(y) \neq 0$.

The value of n determines the minimum number of readouts that has to be taken in order to assess the growth rate μ with the requested maximum allowable standard deviation $\sigma_\mu$. Embodiments of the minimum number n of readouts are 13 or more readouts, 100 or more, 1,000 or more readouts, 5,000 or more readouts, 10,000 or more readouts, or 100,000 or more readouts. The more readouts are taken the more the frequency can be increased, i.e. the time interval between two consecutive readouts can be reduced and thus, the overall measuring time can be kept low, preferably in a range of 4 hours or below. Furthermore, the precision may be increased by using increasing the number n of readouts and the frequency $f$.

The precision of the inventive method may furthermore be increased by using two or more compartments, preferably 100 or more, more preferably 1000 or more compartments comprising the same test assay. In this respect more than one carrier may sequentially or simultaneously, preferably simultaneously be used for the inventive method. Then one or more slopes of linear trends α in step e) of the inventive method is estimated by averaging the distribution of a difference from a subtraction of constituents of a pair of readout values $\{x_i\}$ and $\{x_j\}$ where j>i divided by the time interval $\delta t_{11}$ between taking readouts indexed i and j of the respective test assays, whereby part or all of then readout values $\{x_i\}$, but at least 13 or more readout values $\{x_i\}$ at corresponding recording times $\{t_i\}$ are used for the distribution. In case, e.g., the carrier comprises 10 different concentrations of an antimicrobial agent or a combination of antimicrobial agents, than the $\frac{1}{10}^{th}$ compartments of the one or more carriers may comprise the same test assay.

The aforementioned embodiments of the first aspect of the present invention may be combined throughout. In particular the different preferred embodiments of the first aspect of the present invention can be combined with each other.

All aforementioned embodiments including the combination of preferred embodiments in relation to the first aspect of the present invention can also be used for the second aspect of the present invention.

The second aspect of the present invention relates to a rapid antimicrobial susceptibility testing system for performing a phenotypic antimicrobial susceptibility test (AST) using broth dilution, the system comprising:

a) an incubation assembly adapted to house at least one carrier having one or more compartments for receiving a sample of a microorganism inoculum diluted in a growth medium, wherein the or at least part of the compartments comprise respectively a single antimicrobial agent or a combination of antimicrobial agents, so that each compartment houses a respective test assay, wherein the incubation assembly is configured to provide an incubation and/or measuring environment of the one or more test assays in the one or more compartments, b) an interrogation and readout assembly comprising interrogation means and measuring means configured to interrogate and readout the one or more test assays during incubation of the one or more carriers, wherein the interrogation and readout assembly facilitates i) measuring at least n times for each of the one or more test assays, with constant or inconstant frequency $f$, a signal derived from a chemical or physical property of the inoculated microorganism, wherein the signal represents an essentially monotonic function of the number of the microorganisms in the measured test assay, and ii) reading out corresponding values $\{x_i\}$ at corresponding recording times $\{t_i\}$, wherein i represents the index number of the measurement represented by an integer 1 to n, and wherein n represents a full integer of 13 or more measurements, and c) a computing assembly comprising one or more processors and one or more computer-readable media storing instructions that, when executed by the one or more processors, cause the one or more processors to perform operations comprising i) receiving from the interrogation and readout assembly the number n of readouts, the values $\{x_i\}$ and corresponding recording times $\{t_i\}$ and ii) estimating one or more slopes of linear trends α in data as a function of distribution of a difference from a subtraction of constituents of a pair of readout values $\{x_i\}$ and $\{x_j\}$, where j>i, divided by the time interval $\delta t_{11}$ between taking readouts indexed i and j, whereby part or all of the n readout values $\{x_i\}$, but at least 13 or more readout values $\{x_i\}$ at corresponding recording times 43 are used for the distribution, and iii) determining the qualitative or quantitative susceptibility of the inoculated microorganism against the single antimicrobial agent or the combination of antimicrobial agents as a function of one or more slopes of linear trends α.

As already disclosed with respect to the first aspect of the present invention the incubation assembly may be adapted to comprise more than one carrier simultaneously, preferably 10 or more, or 100 or more. This may be facilitated with suitable means presented by the prior art, such as a nest assembly adapted to house at least one carrier, preferably 10 or more, or 100 or more carriers having one or more compartments respectively. In case of multiple carriers, the carrier may preferably be a microfluidic chip, more preferably a microfluidic chip disclosed in Polish patent applications PL 425106 and PL 425107.

As already disclosed with respect to the first aspect of the present invention, the incubation assembly is configured to provide a suitable incubation and/or measuring environment for the test assays of the one or more carriers contained therein. In the context of the present invention, the expression "suitable incubation environment" means that optimal conditions for growth of the microorganism are provided, e.g., temperature in the range of 30 to 40° C., preferably 35 to 37° C., exchange of gases, in particular oxygen for aerobic microorganisms, etc. The suitable incubation environment may be provided by the incubation assembly and/or the carrier, such as a microfluidic chip, preferably the microfluidic chip as described in PL 425107. In the context of the present invention the expression "suitable measuring environment" means that the incubation assembly and the carrier allows for interrogating the one or more test assays comprised in the compartment(s) of the carrier and measuring the essentially monotonically correlated property/signal. In case the intensity of light (scattered light, fluorescence) is measured, the incubation assembly is preferably separated from light not emitted by the test assays, i.e. in other words the test assay is kept dark.

According to one embodiment of the second aspect of the present invention, the interrogation and readout assembly comprises interrogation means and measuring means configured to interrogate and readout the one or more test assays during incubation of the one or more carriers. In particular the interrogation and readout assembly may preferably comprise an optical assembly, which is configured to interrogate and readout at least one of intensity of light, e.g., fluorescence or scattered light; optical density, absorbance, turbidity, light reflection or other optical properties; conductivity, capacitance or other electrical properties; partial pressures of gases involved in metabolism of the microorganism, viscosity or nutrient uptake of the test assay during incubation.

The interrogation and readout assembly facilitates i) measuring at least n times for each of the one or more test assays, with constant or inconstant frequency $f$, a signal derived from a chemical or physical property of the inoculated microorganism, wherein the signal represents an essentially monotonic function of the number of the microorganisms in the measured test assay, and ii) reading out corresponding values $\{x_i\}$ at corresponding recording times $\{t_i\}$, wherein i represents the index number of the measurement represented by an integer 1 to n, and wherein n represents a full integer of 13 or more measurements.

The Tables 1, 2, and 3 show the minimum number of readouts required to provide the assessment of the one or more slopes of linear trends with the requested resolution, defined as the ratio of the standard deviation of the estimate of linear trend multiplied by the total time of experiment to the high-frequency noise of the measuring system. The said resolution can be preferably achieved with 95% confidence (Table 1), 90% confidence (Table 2), and 70% confidence (Table 3). The tables show the values of preferred constant frequencies of signals required to provide the assessment of trend with requested resolution in the given time of experiment.

TABLE 1

| | | resolution | | | | |
|---|---|---|---|---|---|---|
| | | 1% | 5% | 10% | 50% | 100% |
| | | | | $n_{min}$ | | |
| | | 120000 | 4800 | 1200 | 48 | 12 |
| time span of experiment | 0.5 h | 66.7 Hz | 2.67 Hz | 667 mHz | 26.7 mHz | 6.67 mHz |
| | 1.0 h | 33.3 Hz | 1.33 Hz | 333 mHz | 13.3 mHz | 3.33 mHz |
| | 1.5 h | 22.2 Hz | 889 mHz | 222 mHz | 8.89 mHz | 2.22 mHz |
| | 2.0 h | 17.7 Hz | 667 mHz | 167 mHz | 6.67 mHz | 1.67 mHz |
| | 2.5 h | 13.3 Hz | 533 mHz | 133 mHz | 5.33 mHz | 1.33 mHz |
| | 3.0 h | 11.1 Hz | 444 mHz | 111 mHz | 4.44 mHz | 1.11 mHz |
| | 3.5 h | 9.52 Hz | 381 mHz | 95.2 mHz | 3.81 mHz | 0.95 mHz |
| | 4.0 h | 8.33 Hz | 333 mHz | 83.3 mHz | 3.33 mHz | 0.83 mHz |

Table 1 shows the minimum number $n_{min}$ of readouts required to assess the linear trend in data with a given resolution with 95% confidence (k=3). The frequencies of taking readouts for preferred times of experiments are also given.

TABLE 2

| resolution<br>$n_{min}$ | | 1%<br>53333 | 5%<br>2133 | 10%<br>533 | 50%<br>21 |
|---|---|---|---|---|---|
| Time | 0.5 h | 29.6 Hz | 1.19 Hz | 296 mHz | 11.9 mHz |
| span | 1.0 h | 14.8 Hz | 593 mHz | 148 mHz | 5.93 mHz |
| of | 1.5 h | 9.88 Hz | 395 mHz | 98.8 mHz | 3.95 mHz |
| experiment | 2.0 h | 7.41 Hz | 296 mHz | 74.1 mHz | 2.96 mHz |
| | 2.5 h | 5.93 Hz | 237 mHz | 59.3 mHz | 2.37 mHz |
| | 3.0 h | 4.94 Hz | 198 mHz | 49.4 mHz | 1.98 mHz |
| | 3.5 h | 4.23 Hz | 169 mHz | 42.3 mHz | 1.69 mHz |
| | 4.0 h | 3.70 Hz | 148 mHz | 37.0 mHz | 1.48 mHz |

Table 2 shows the minimum number $n_{min}$ of readouts required to assess the linear trend in data with a given resolution with 90% confidence (k=2). The frequencies of taking readouts for preferred times of experiments are also given.

TABLE 3

| resolution<br>$n_{min}$ | | 1%<br>13333 | 5%<br>533 | 10%<br>133 |
|---|---|---|---|---|
| time | 0.5 h | 7.41 Hz | 296 mHz | 74.1 mHz |
| span | 1.0 h | 3.70 Hz | 148 mHz | 37.0 mHz |
| of | 1.5 h | 2.47 Hz | 98.8 mHz | 24.7 mHz |
| experiment | 2.0 h | 1.85 Hz | 74.1 mHz | 18.5 mHz |
| | 2.5 h | 1.48 Hz | 59.3 mHz | 14.8 mHz |
| | 3.0 h | 1.23 Hz | 49.4 mHz | 12.3 mHz |
| | 3.5 h | 1.06 Hz | 42.3 mHz | 10.6 mHz |
| | 4.0 h | 926 mHz | 37.0 mHz | 92.6 mHz |

Table 3 shows the minimum number $n_{min}$ of readouts required to assess the linear trend in data with a given resolution with 70% confidence (k=1). The frequencies of taking readouts for preferred times of experiments are also given.

The analysing function has been discussed in detail with respect to the first aspect of the present invention, which embodiments including combination of preferred embodiments also apply to the second aspect of the present invention.

Furthermore, the rapid antimicrobial susceptibility testing system of the second aspect of the present invention comprises a computing assembly. This computing assembly comprises one or more processors and one or more computer-readable media storing instructions that, when executed by the one or more processors, cause the one or more processors to perform operations comprising i) receiving from the interrogation and readout assembly the number n of readouts, the values $\{x_i\}$ and corresponding recording times $\{t_i\}$ and ii) estimating one or more slopes of linear trends α in data as a function of distribution of a difference from the subtraction of constituents of a pair of readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times 43 are used for the distribution, and iii) determining the qualitative or quantitative susceptibility of the inoculated microorganism against the single antimicrobial agent or the combination of antimicrobial agents as a function of one or more slopes of linear trends α.

The computing means may be provided by, e.g., a computer, a laptop, a smart device, or—in case the inventive assembly is connected to the internet—by an internet-based server, in particular an internet-based cloud computing network.

Again, the analysing function has been discussed in detail with respect to the first aspect of the present invention, which embodiments including combination of preferred embodiments also apply to the second aspect of the present invention.

According to one embodiment of the second aspect of the present invention, the computing assembly is further configured to perform estimation and determination operations after each 10 measurements, preferably after each 5 measurements, more preferably after each single measurement. The quicker the performance of the estimation and determination operations are conducted, the quicker the results are provided, in particular they may be provided in real time. However, with increasing estimation and determination operations, e.g. after each single measurement, the processing capacity is increased and accordingly a suitable processing device needs to be used for the inventive system.

According to another preferred embodiment of the second aspect of the present invention the computing assembly is further configured to estimate one or more slopes of linear trends α with a predetermined standard deviation $\sigma_\alpha$ by calculating the minimum number of readouts n as a function of a standard deviation σ of a high frequency noise of the measuring means and time interval δt between consecutive readouts. The estimation is already described in detail with respect to the first aspect of the present invention and all embodiments thereof including the combination of preferred embodiments also apply to the second aspect of the present invention.

According to the third aspect of the present invention the use of the inventive rapid antimicrobial susceptibility testing system for performing a phenotypic antimicrobial susceptibility test (AST) using broth dilution of the second aspect of the present invention in determining qualitative and quantitative susceptibility of inoculated microorganism is disclosed. All embodiments including combination of preferred embodiments of the first and second aspects of the present invention also apply to the third aspect of the present invention.

In addition to the above disclosed aspects of the present invention, namely the use of the estimation and determination analysis according to method steps e) and f) of the first aspect of the present invention for assessing growth of microorganisms, the inventive analysis method can also be used for monitoring slow processes which progress essentially monotonically correlates with a measurable property (signal), such as a monitoring i) the progress of a (slow) chemical reaction, ii) the wear of parts in particular mechanical parts, and iii) rare events, such as counting particles in nuclear reactions. A person skilled in the art will readily be able to amend the respective environments according to the other processes used. The inventive analyzing method including estimation and determination as set out for the first and second aspect of the present invention can also be applied for the other methods.

The present invention relates also to methods and systems for rapidly testing antimicrobial susceptibility, wherein the qualitative and quantitative susceptibility of an inoculated microorganism against an antimicrobial agent or a combination of antimicrobial agents is determined as a function of one or more slopes of linear trends α of readouts values. However, it can be also used for the assessment of any increase in the recorded data, and is particularly advantageous if the increase is slow and the high-frequency noise of the measuring means is high. For example, the invention can be used to facilitate the measurement of wear rate of mechanical parts (Tony L. Schmitz Jason E. Action David L. Burris John C. Ziegert W. Gregory Sawyer, Wear-Rate Uncertainty Analysis, Journal of Tribology, Vol. 126, OCTOBER 2004, 802-807, DOI: 10.1115/1.1792675, Niklas Axén, Sture Hogmark, Staffan Jacobson, Friction and Wear Measurement Techniques, 2001, http://home.ufam.edu.br/berti/nanomateriais/8403_PDF_CH13.pdf), where the volume and/or weight loss of a mechanical part or sample is low. As the decrease is typically linear with the number of tested cycles, it can be assessed using the present invention. Also, the uncertainty of such measurement is lower than typical methods (i.e. spread of the average result from many repetitions of the same experiment) thanks to the scaling $n^{-3/2}$ with the number of readouts (tested cycles).

Another application of the present invention is the monitoring of the progress of slow chemical reactions, including rusting, which causes a change of weight of the sample, or the monitoring of the chemical reactions at the early stage, i.e. the monitoring of the progress of Polymerase Chain Reaction (Bartlett, J. M. S.; Stirling, D. (2003). "A Short History of the Polymerase Chain Reaction". PCR Protocols. Methods in Molecular Biology. 226 (2nd ed.). pp. 3-6, A. A. Morley. Digital PCR: A brief history. Biomolecular Detection and Quantification, 1(1):1-2, 2014, J. F. Huggett, S. Cowen, C. A. Foy, Considerations for digital PCR as an accurate molecular diagnostic tool, Clinical Chemistry, 61 (1), 79-88, 2015) or Loop-mediated isothermal amplification (Notomi T, Okayama H, Masubuchi H, Yonekawa T, Watanabe K, Amino N, Hase T (2000). "Loop-mediated isothermal amplification of DNA". Nucleic Acids Res. 28 (12): E63) reactions, which facilitate the detection and quantitation of nucleic acids.

The present invention is described in the following on the basis of Figures and exemplary embodiments, which merely serve as examples and which shall not limit the scope of the present protective right.

DETAILED DESCRIPTION OF THE FIGURES

FIG. 1 shows an exemplary growth curve of a sample microorganism in an antimicrobial susceptibility test (further described in Executive Example 1), where a dashed line indicates the end of the phase of growth wherein the changes of measured signal value due to the microbial population growth are smaller than the changes of the signal value due to the high-frequency noise of the measuring means. The growth curve was measured experimentally. The broth dilution with microorganisms and antibiotic was incubated in a compartment of a microfluidic chip disclosed in Polish patent applications PL 425106 and PL 425107 and exposed to light during the incubation. The intensity of scattered light was measured by means of the digital camera. The total intensity of the scattered light was assessed by integrating light intensity from the pixels corresponding to the area of the compartment.

Figure 2:
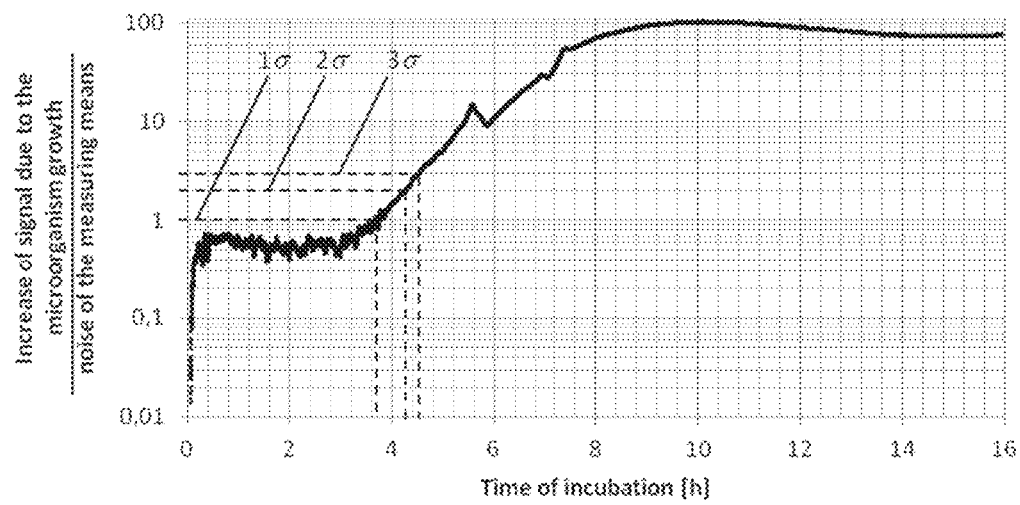
FIG. 2 shows the increase of signal values (values of readout) due to the growth of microorganisms as a multiplicity of the high-frequency noise of the measuring means, wherein the points of 1-fold, 2-fold and 3-fold increase of signal over the high-frequency noise of measuring means are indicated by dashed lines 1σ, 2σ, and 3σ.

FIG. 2 shows the increase of signal values (values of readout) due to the growth of microorganisms as a multiplicity of the high-frequency noise of the measuring means, wherein the points of 1-fold, 2-fold and 3-fold increase of signal value over the high-frequency noise of measuring means are indicated by dashed lines. The bigger is the increase with respect to the high-frequency noise, the more confidently can the increase of the signal be assessed.

Figure 3:
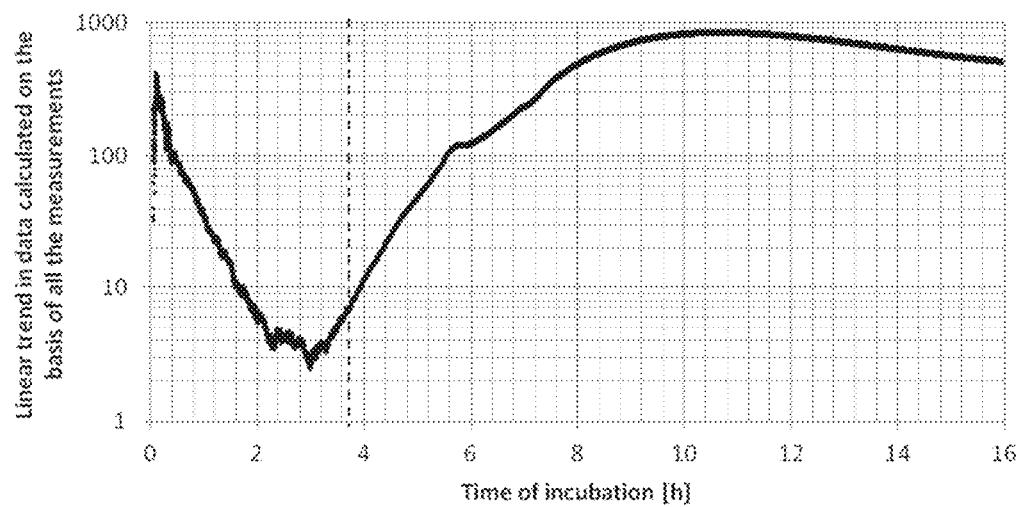
FIG. 3 shows the value of the linear trend α calculated for the exemplary growth curve using the inventive method using all measured values, wherein a dashed line indicates the end of the phase of growth wherein the changes of measured signal value due to the microbial population growth are smaller than the changes of the signal value due to the high-frequency noise of the measuring means.

FIG. 3 shows the value of the linear trend $\alpha$ calculated for the exemplary growth curve shown in FIG. 1 using the inventive method using all measured values, wherein a dashed line indicates the end of the phase of growth wherein the changes of measured signal value due to the microbial population growth are smaller than the changes of the signal value due to the high-frequency noise of the measuring means. The linear trend $\alpha$ was calculated as the average value of the subtraction of two readouts (earlier readout was subtracted from the later readout) divided by the time interval between taking the two readouts, from all the pairs of readouts recorded from the beginning of the experiment.

Figure 4:
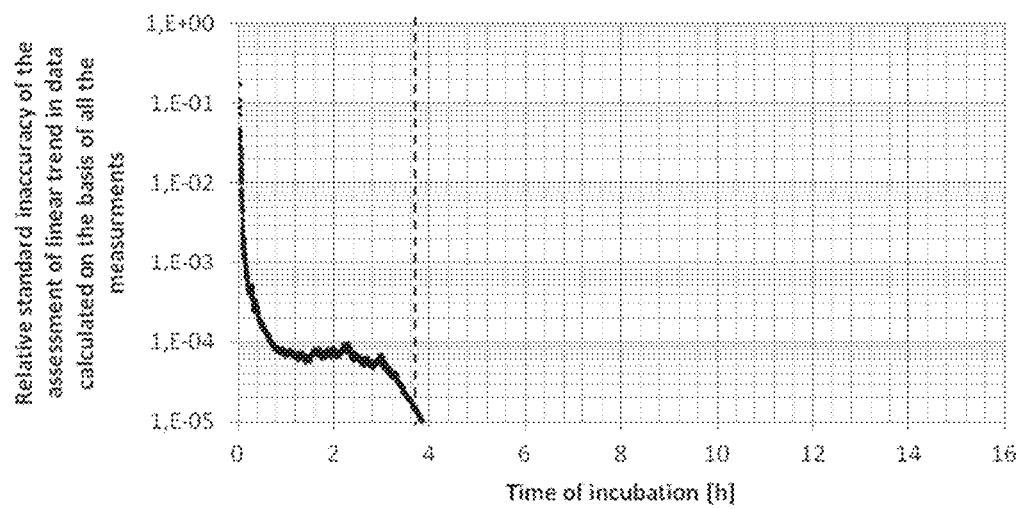
FIG. 4 shows the relative uncertainty (standard deviation of the estimate) of the trend α using the inventive method calculated with all measured values, wherein a dashed line indicates the end of the phase of growth wherein the changes of measured signal value due to the microbial population growth are smaller than the changes of the signal value due to the high-frequency noise of the measuring means.

FIG. 4 shows the relative uncertainty (standard deviation of the estimate) of the trend $\alpha$ calculated for the exemplary growth curve shown in FIG. 1 using the inventive method using all measured values, wherein a dashed line indicates the end of the phase of growth wherein the changes of measured signal value due to the microbial population growth are smaller than the changes of the signal value due to the high-frequency noise of the measuring means. The linear trend $\alpha$ was calculated as the average value of the subtraction of two readouts (earlier readout was subtracted from the later readout) divided by the time interval between taking the two readouts, from all the pairs of readouts recorded from the beginning of the experiment. The uncertainty was calculated as the standard deviation of the estimate of the average value of subtraction product.

Figure 5:
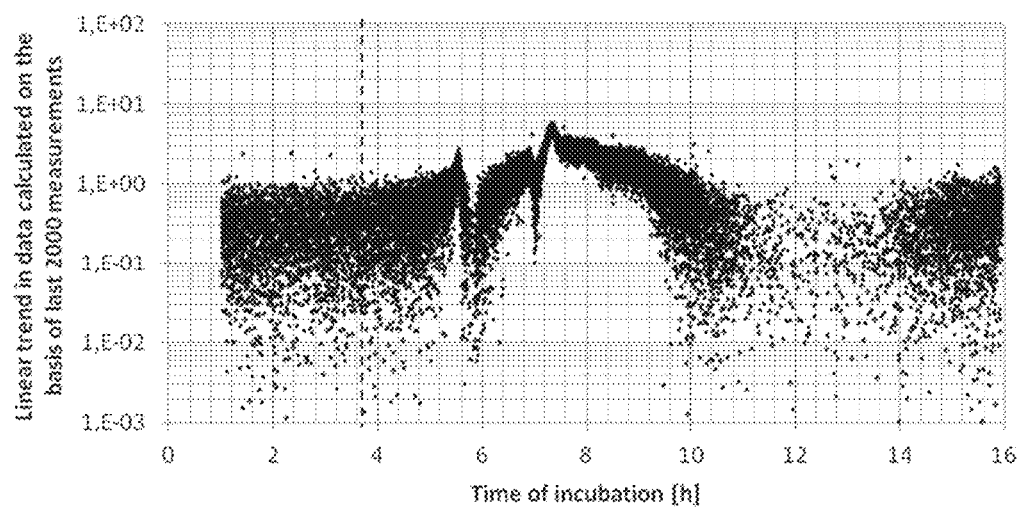
FIG. 5 shows the value of the linear trend α calculated for the exemplary growth curve using the inventive method and the last 2000 measurements taken, wherein a dashed line indicates the end of the phase of growth wherein the changes of measured signal value due to the microbial population growth are smaller than the changes of the signal value due to the high-frequency noise of the measuring means.

FIG. 5 shows the value of the linear trend $\alpha$ calculated for the exemplary growth curve shown in FIG. 1 using the inventive method and the last 2000 measurements taken, wherein a dashed line indicates the end of the phase of growth wherein the changes of measured signal value due to the microbial population growth are smaller than the changes of the signal value due to the high-frequency noise of the measuring means. The linear trend $\alpha$ was calculated as the average value of the product of subtraction of two readouts (earlier readout was subtracted from the later readout) divided by the time interval between taking the two readouts, from all the pairs created from last 2000 readouts recorded.

Figure 6:
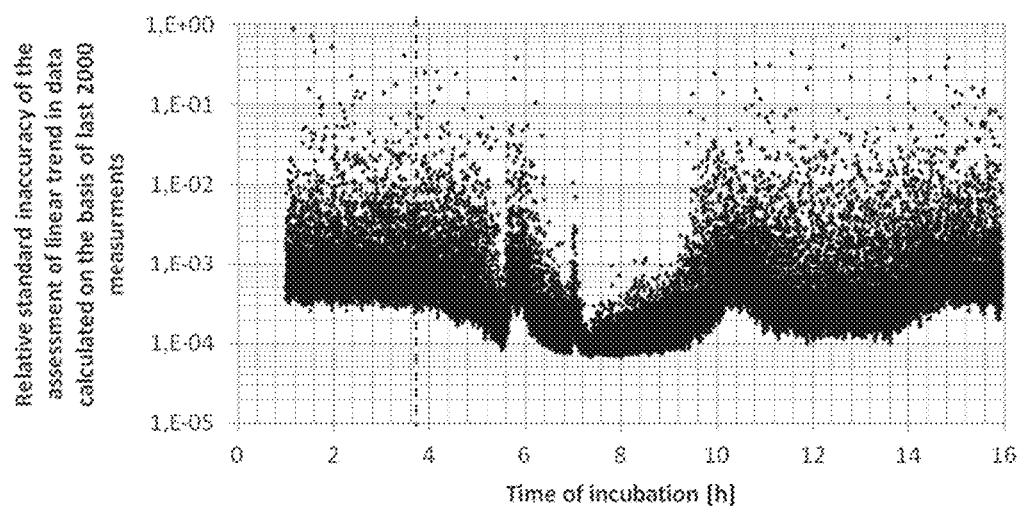
FIG. 6 shows the relative uncertainty (standard deviation of the estimate) of the trend α calculated using the inventive method and the last 2000 measurements taken, wherein a dashed line indicates the end of the phase of growth wherein the changes of measured signal value due to the microbial population growth are smaller than the changes of the signal value due to the high-frequency noise of the measuring means.

FIG. 6 shows the relative uncertainty (standard deviation of the estimate) of the trend $\alpha$ calculated using the inventive method and the last 2000 measurements taken, wherein a dashed line indicates the end of the phase of growth wherein the changes of measured signal value due to the microbial population growth are smaller than the changes of the signal value due to the high-frequency noise of the measuring means. The linear trend $\alpha$ was calculated as the average value of the product of subtraction of two readouts (earlier readout was subtracted from the later readout) divided by the time interval between taking the two readouts, from all the pairs created from last 2000 readouts recorded. The uncertainty was calculated as the standard deviation of the estimate of the average value of subtraction product (difference).

Figure 7:
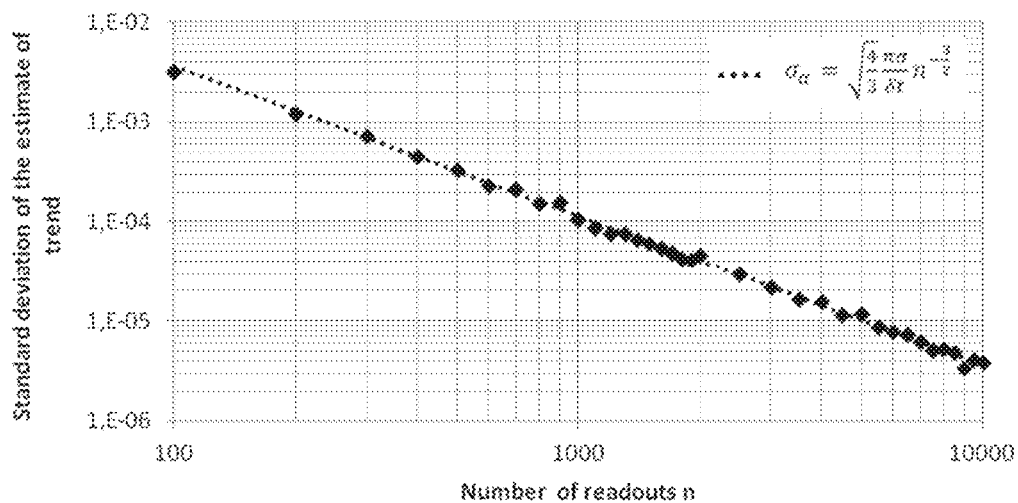
FIG. 7 shows a dependence of a standard deviation of an estimated slope of trend α on a number of readouts.

FIG. 7 shows a dependence of a standard deviation of estimated slopes of trends $\alpha$ on a number of readouts. The graph was obtained by means of Monte-Carlo simulations, where every point (standard deviation of the estimate) was calculated from 1000 repetitions of the simulation in for the same input conditions. The behavior of the uncertainty resembles the formula obtained analytically and scales with the number n of readouts with the function $$n^{-\frac{3}{2}}.$$

Figure 8:
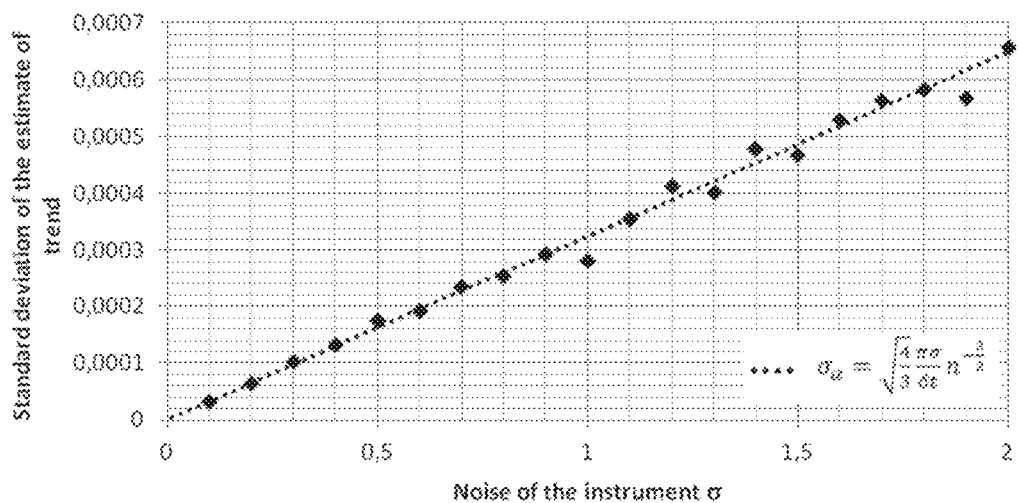
FIG. 8 shows a dependence of a standard deviation of an estimated slope of trend α on a high-frequency noise of the measuring device

FIG. 8 shows a dependence of a standard deviation of estimated slopes of trends $\alpha$ on a high-frequency noise of the measuring device. The graph was obtained by means of Monte-Carlo simulations, where every point (standard deviation of the estimate) was calculated from 1000 repetitions of the simulation in for the same input conditions. The behavior of the uncertainty resembles the formula obtained analytically and scales linearly with the standard deviation of the high-frequency noise σ of the instrument.

Figure 9:
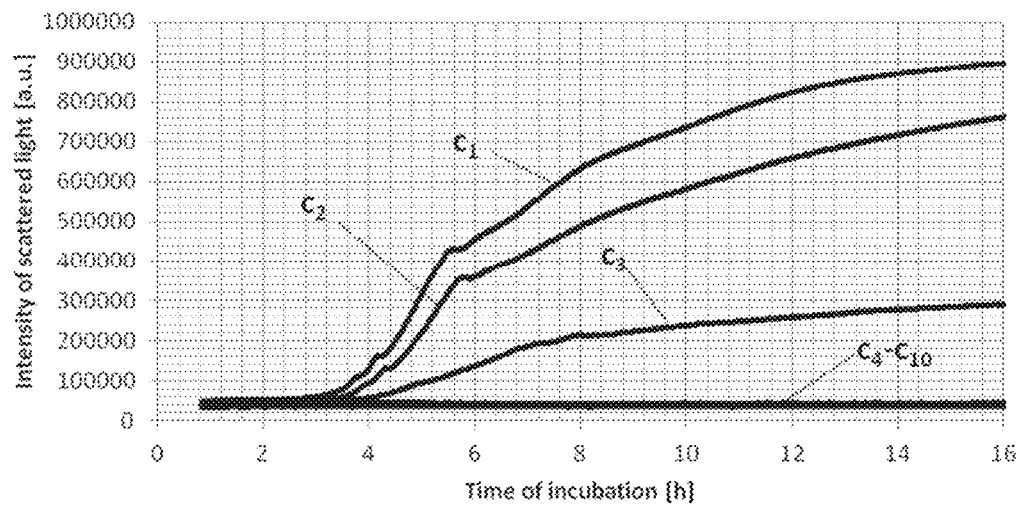
FIG. 9 shows ten growth curves from separate test assays of an antimicrobial susceptibility test using different antimicrobial concentrations in order to determine the minimum inhibitory concentration.

FIG. 9 shows ten growth curves from separate test assays of an antimicrobial susceptibility test using different antimicrobial concentrations in order to determine the minimum inhibitory concentration. The growth curves were recorded experimentally, and the procedure is described in Executive Example 1. The concentrations of antibiotic, having the symbols $c_1$ to $c_{10}$, are described in Table 4 in Executive Example 1. Because of the high frequency noise of the measuring device, the curves overlap at the beginning (first 4 hours) of incubation.

Figure 10:
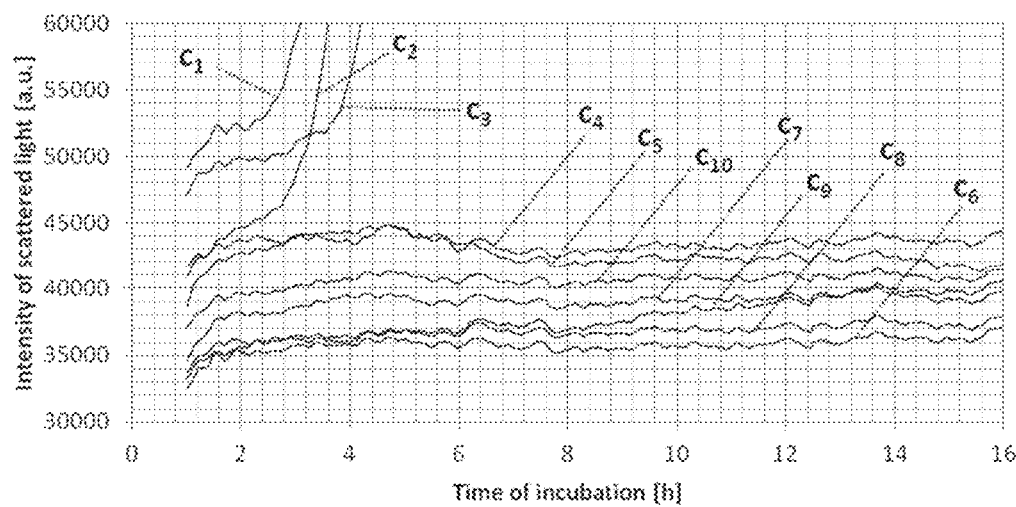
FIG. 10 shows ten growth curves from ten separate test assays of an antimicrobial susceptibility test using different antimicrobial concentrations in order to determine the minimum inhibitory concentration.

FIG. 10 shows ten growth curves from separate test assays of an antimicrobial susceptibility test using different antimicrobial concentrations in order to determine the minimum inhibitory concentration. The growth curves were recorded experimentally, and the procedure is described in Executive Example 1. The scale on the axis of intensity of scattered light was narrowed and instead of the recorded signals, the simple moving average curves (means of previous 200 readouts) were drawn to distinguish between the growth curves. The concentrations of antibiotic, having the symbols $c_1$ to $c_{10}$, are described in Table 4 in Executive Example 1.

Figure 11:
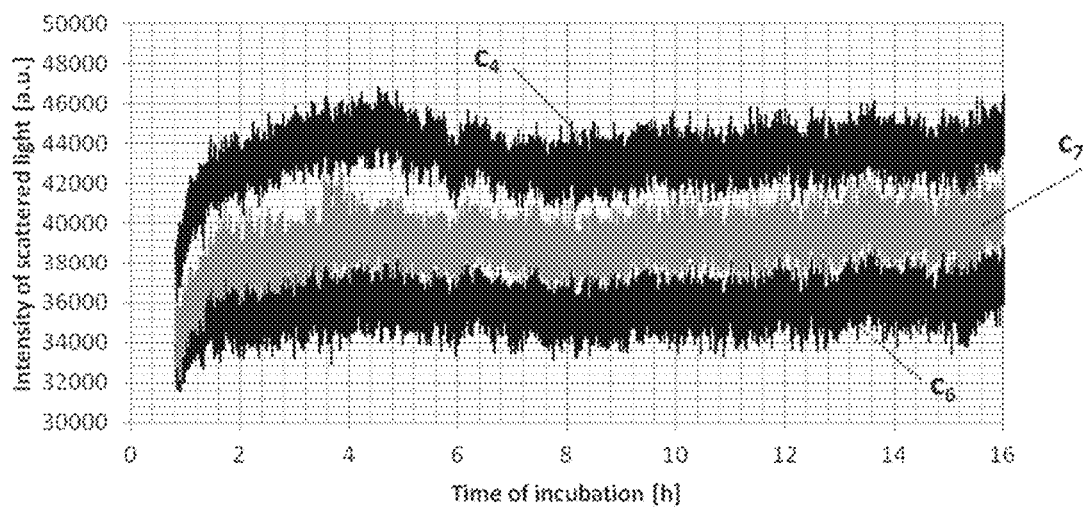
FIG. 11 shows three growth curves from three separate test assays of an antimicrobial susceptibility test using different antimicrobial concentrations in order to determine the minimum inhibitory concentration.

FIG. 11 shows three growth curves from separate test assays of an antimicrobial susceptibility test using different antimicrobial concentrations in order to determine the minimum inhibitory concentration. The growth curves were recorded experimentally, and the procedure is described in Executive Example 1. The concentrations of antibiotic, having the symbols $c_4$, $c_6$, and $c_7$ are described in Table 4 in Executive Example 1. Because of the high frequency noise of the measuring device, the curves overlap.

Figure 12:
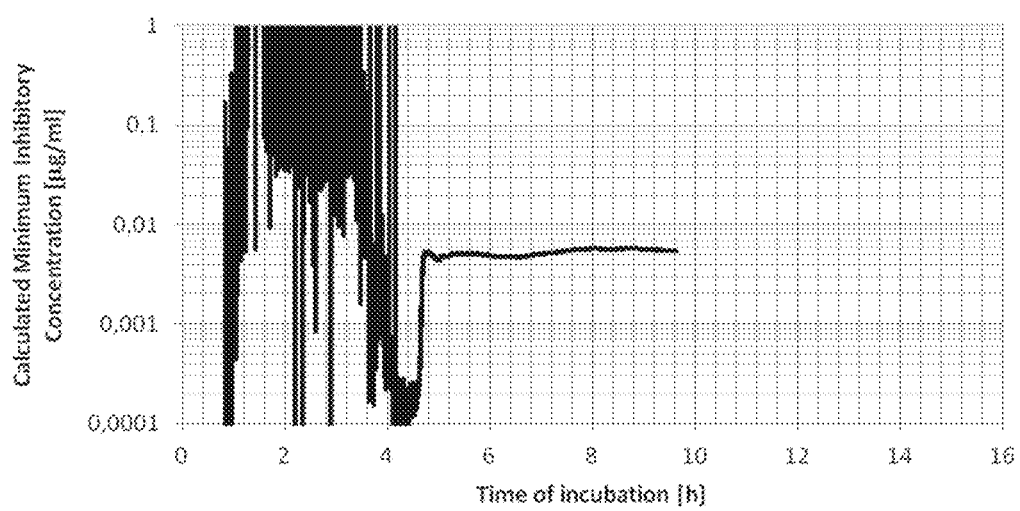
FIG. 12 shows the evolution of the value of MIC determined experimentally with the use of state-of art methods.

FIG. 12 shows the evolution of the value of Minimum Inhibitory Concentration (MIC) determined experimentally with the use of state-of art methods as described in Executive Example 1. The value of Minimum Inhibitory Concentration saturates after 5 hours of incubation when positive growth curves are clearly distinguishable from negative growth curves.

Figure 13:
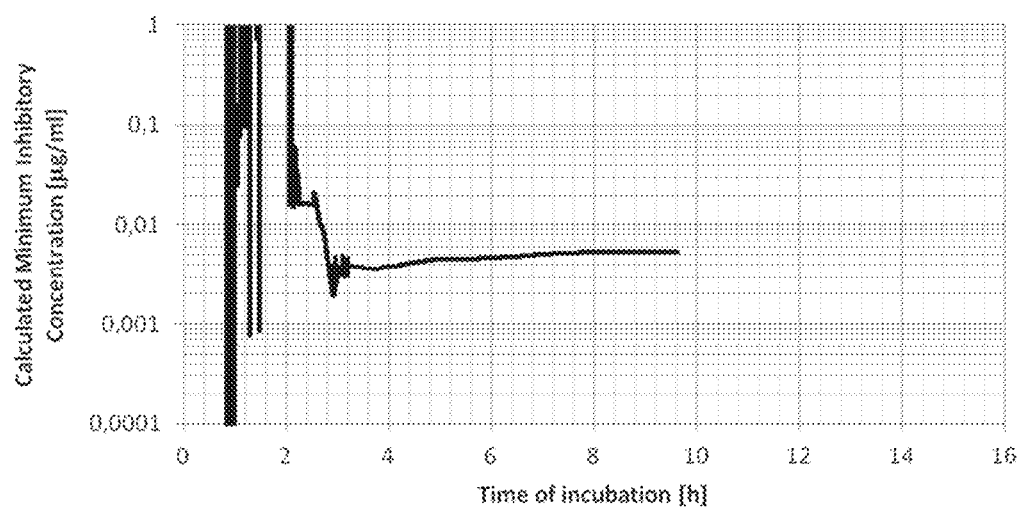
FIG. 13 shows the evolution of the value of MIC determined experimentally with the use of the presented invention.

FIG. 13 shows the evolution of the value of MIC determined experimentally with the use of the presented invention as described in Executive Example 1. The value of Minimum Inhibitory Concentration saturates after 3 hours of incubation when positive growth curves are still not distinguishable from negative growth curves.

Figure 14:
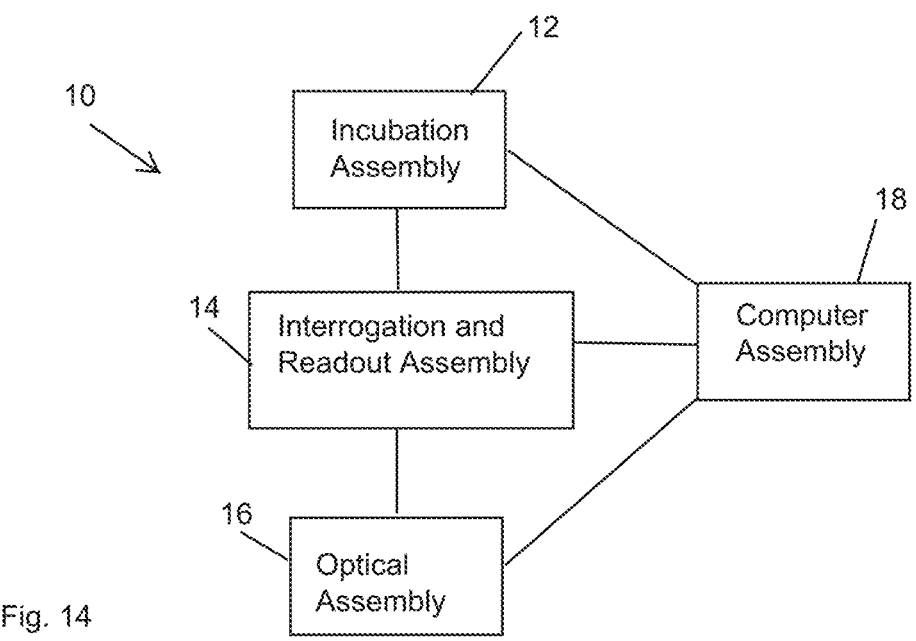
FIG. 14 schematically illustrates a rapid antimicrobial susceptibility testing system for performing a phenotypic antimicrobial test (AST) according to the present invention.

FIG. 14 illustrates a rapid antimicrobial susceptibility testing system for performing a phenotypic antimicrobial test (AST) according to the present invention. The system 10 includes an incubation assembly 12 to house at least one carrier having one or more compartments for receiving a sample of a microorganism inoculum diluted in a growth medium; an interrogation and readout assembly 14 comprising interrogation means and measuring means configured to interrogate and readout the one or more test assays during incubation of the one or more carriers; an optical assembly 16 configured to interrogate and readout at least, one of intensity of light; optical density, absorbents, turbidity, light reflection or other optical properties; and a computing assembly 18 comprising one or more processors and one or more computer readable media storage instructions that, when executed by the one or more processors cause the one or more processors to perform operations as described.

EXAMPLES

Executive Example 1

The present invention for rapidly testing antimicrobial susceptibility was used to determine quantitatively the Minimum Inhibitory Concentration of ciprofloxacin. The Antimicrobial Susceptibility Test was prepared to test the range of antibiotic concentrations required by EUCAST and CLSI standards (The European Committee on Antimicrobial Susceptibility Testing. Routine and extended internal quality control for MIC determination and disk diffusion as recommended by EUCAST. Version 8.0, 2018. http://wwvv.eucastorg; Performance Standards for Antimicrobial Susceptibility Testing, 22th Edition; CLSI document M100-S22. Wayne, PA: Clinical and Laboratory Standard Institute; 2012).

The assessment was executed in the following steps.
1. The series of dilutions of antibiotic (ciprofloxacin) in an appropriate broth (i.e. Cation Adjusted Mueller-Hinton II Broth) was prepared; the dilutions were two-fold (i.e. 0.25; 0.5; 1.0; 2.0; 4.0; 8.0 mg/l) and cover the range of antibiotic concentrations indicated in standards: EUCAST and CLSI. The concentrations of antibiotic in prepared series were twice as high as the target concentrations because they were subsequently mixed with bacteria (*Escherichia coli* ATCC 25922) sample in 1:1 ratio. The target concentrations of antibiotic are presented in the table 4 below.

| Symbol of dilution | concentration |
|---|---|
| c1: | 0.0009765625 mg/l |
| c2: | 0.001953125 mg/l |
| c3: | 0.00390625 mg/l |
| c4: | 0.0078125 mg/l |
| c5: | 0.015625 mg/l |
| c6: | 0.03125 mg/l |
| c7: | 0.0625 mg/l |
| c8: | 0.125 mg/l |
| c9: | 0.25 mg/l |
| c10: | 0.5 mg/l |

Table 4 shows the concentrations of antibiotic (ciprofloxacin) used in the experiment. The suspension of microorganisms (bacteria) of the density of $10^6$ CFU/ml (Colony Forming Units/ml) was prepared.

2. The equal portions (i.e. 100 μl) of the suspension of microorganisms and selected dilution of antibiotic were mixed in a well of a multi-well plate (i.e. Corning® 96 Well CellBIND® Microplate, https://www.sigmaaldrich.com/catalog/product/sigma/cls3340, Corning™ Costar™ Flat Bottom Cell Culture Plates, https://www-.fishersci.com/shop/products/costar-cell-culture-plates-17/0720090) that allowed for the measurement of the optical properties of the sample. For each concentration of antibiotic, 8 repetitions were prepared.

3. The plate was incubated for 16 h in 35° C., and the intensity of light scattered by the contents of each well was recorded during the progress of the experiment. The growth curves recorded are shown in FIGS. 9 to 11.

4. For each well, a series of readouts was recorded, and then each series of readouts was analyzed simultaneously and independently in the following steps:

a. For every two recorded values, the difference from a subtraction of the earlier value from the latter value, divided by the time interval between taking the two readouts, was calculated.
b. The average a of the differences was being calculated during the progress of the experiment for all the pairs of recorded readouts. It was calculated in arbitrary units. The calculated average was equal to the linear trend in recorded data, i.e. the slope of the series of readouts.
c. It was assumed, that the increase of the recorded signal values was caused by the growth of bacteria, therefore, the growth rate of bacteria was assumed to be equal to the slope of the series of readouts.
d. The calculated values of linear trend in data were given as the function of antibiotic concentration.
e. The function was fitted with the double-exponential Gompertz function (Zwietering, M. H.; Jongenburger, I.; Rombout, F. M.; van 't Riet, K. (1990), "Modeling of the Bacterial Growth Curve", Applied and Environmental Microbiology, 56 (6): 1875-1881).
f. The value of Minimum Inhibitory Concentration was determined as: the crossing of the line tangent to the growth rate vs. antibiotic concentration dependence at the point of highest slope (Chorianopoulos, N. G., Lambert, R. J. W., Skandamis, P. N., Evergetis, E. T., Haroutounian, S. A. and Nychas, G.-J. E. (2006), A newly developed assay to study the minimum inhibitory concentration of Satureja spinosa essential oil. Journal of Applied Microbiology, 100: 778-786. doi: 10.1111/j.1365-2672.2006.02827.x; Lambert, R. J. W. and Pearson, J. (2000), Susceptibility testing: accurate and reproducible minimum inhibitory concentration (MIC) and non-inhibitory concentration (NIC) values. Journal of Applied Microbiology, 88: 784-790. doi:10.1046/j.1365-2672.2000.01017.x; Lambert, R. J. W. and Lambert, R. (2003), A model for the efficacy of combined inhibitors. Journal of Applied Microbiology, 95: 734-743. doi:10.1046/j.1365-2672.2003.02039.x) and compared to the reference value. The calculated values of Minimum Inhibitory Concentration and their time evolution are given in FIG. 13.
g. For the reference, the values of Minimum Inhibitory Concentration were calculated using state-of-art method, i.e. the end-point value of the recorded signal. The last values of recorded signal were also given as the function of antibiotic concentration to provide the reference function.
h. The reference function was fitted with the double-exponential Gompertz function (Zwietering, M. H.; Jongenburger, I.; Rombout, F. M.; van 't Riet, K. (1990), "Modeling of the Bacterial Growth Curve", Applied and Environmental Microbiology, 56 (6): 1875-1881).
i. The value of Minimum Inhibitory Concentration was determined as: the crossing of the line tangent to the growth rate vs. antibiotic concentration dependence at the point of highest slope (Chorianopoulos, N. G., Lambert, R. J. W., Skandamis, P. N., Evergetis, E. T., Haroutounian, S. A. and Nychas, G.-J. E. (2006), A newly developed assay to study the minimum inhibitory concentration of Satureja spinosa essential oil. Journal of Applied Microbiology, 100: 778-786. doi: 10.1111/j.1365-2672.2006.02827.x; Lambert, R. J. W. and Pearson, J. (2000), Susceptibility testing: accurate and reproducible minimum inhibitory concentration (MIC) and non-inhibitory concentration (NIC) values. Journal of Applied Microbiology, 88: 784-790. doi:10.1046/j.1365-2672.2000.01017.x; Lambert, R. J. W. and Lambert, R. (2003), A model for the efficacy of combined inhibitors. Journal of Applied Microbiology, 95: 734-743. doi:10.1046/j.1365-2672.2003.02039.x). The calculated values of Minimum Inhibitory concentration and their time evolution are given in FIG. 12.

The individual features of the aforementioned executive example can separately be inventively combined with the general description of the invention.

The invention claimed is:

1. A computer-implemented method for determining the qualitative or quantitative susceptibility of a microorganism inoculum in a phenotypic antimicrobial susceptibility test (AST) using broth dilution, comprising the following steps:
   a) Providing a microorganism inoculum and diluting the inoculum in a medium suitable for broth dilution AST,
   b) Providing a carrier comprising one or more compartments suitable for broth dilution AST, wherein the or at least part of the compartments comprise respectively a single antimicrobial agent or a combination of antimicrobial agents,
   c) Dispensing a sample of the medium containing the diluted inoculum of step a) into the or at least part of the compartments of the carrier of step b) so that the one or more inoculated compartments of the carrier comprise the respective test assays,
   d) Incubating the carrier of step c) comprising the respective one or more test assays,
   e) Measuring, during the incubation step d), at least n times for each of the one or more test assays with constant or inconstant frequency $f$ a signal derived from a chemical or physical property of the inoculated microorganism, wherein the signal represents an essentially monotonic function of the number of the microorganisms in the measured test assay, and reading out corresponding values $\{x_i\}$ at corresponding recording times $\{t_i\}$, wherein i represents the index number of the measurement represented by an integer 1 to n, and wherein n represents a full integer of 13 or more measurements,
   f) Estimating one or more slopes of linear trends $\alpha$ in data as a function of distribution of a difference from the subtraction of constituents of a pair of the readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times $\{t_i\}$ are used for the distribution, and
   g) Determining the qualitative or quantitative susceptibility of the inoculated microorganism against the single antimicrobial agent or the combination of antimicrobial agents as a function of one or more slopes of linear trends $\alpha$.

2. The computer-implemented method for determining the qualitative or quantitative susceptibility of a microorganism inoculum according to claim 1, wherein in step e) the signal derived from a chemical or physical property of the inoculated microorganism is selected from intensity of light, e.g., fluorescence or scattered light; optical density, absorbance, turbidity, light reflection or other optical properties; conductivity, capacitance or other electrical properties; partial pressures of gases involved in metabolism of the microorganism, viscosity or nutrient uptake.

3. The computer-implemented method for determining the qualitative or quantitative susceptibility of a microorganism inoculum according to claim 1, wherein the microorganism is selected from the group consisting of bacterium, *mycobacterium* and fungus.

4. The computer-implemented method for determining the qualitative or quantitative susceptibility of a microorganism inoculum according to claim 1, wherein the frequency $f$ is preferably 1 mHz or more.

5. The computer-implemented method for determining the qualitative or quantitative susceptibility of a microorganism inoculum according to claim 1, wherein the measurements in step e) are taken at least partially in a phase of microorganism growth, wherein the changes of measured signal value due to the microbial population growth are smaller than the changes of the signal value due to a high-frequency noise of the measurement.

6. The computer-implemented method for determining the qualitative or quantitative susceptibility of a microorganism inoculum according to claim 1, wherein the measurements in step e) are taken in a phase of microorganism growth, wherein the increase in measured signal due to the microorganism growth is equal or less than 3-fold of a high-frequency noise of the measurement.

7. The computer-implemented method for determining the qualitative or quantitative susceptibility of a microorganism inoculum according to claim 1, wherein one or more slopes of linear trends $\alpha$ is/are estimated with a predetermined standard deviation $\sigma_\alpha$ by calculating the minimum number of readouts n as a function of a standard deviation $\sigma$ of a high frequency noise of the measurement and time interval $\delta t$ between consecutive readouts.

8. The computer-implemented method for determining the qualitative or quantitative susceptibility of a microorganism inoculum according to claim 1, wherein two or more compartments comprise the same test assay and one or more slopes of linear trends a in step e) is/are estimated by averaging the distribution of the difference from the subtraction of constituents of a pair of readout values $\{x_i\}$ and $\{x_j\}$, where j>i, divided by the time interval $\delta t_{ij}$ between taking readouts indexed i and j, of the respective test assays.

9. A rapid antimicrobial susceptibility testing system for performing a phenotypic antimicrobial susceptibility test (AST) using broth dilution, the system comprising:
   a) an incubation assembly adapted to house at least one carrier having one or more compartments for receiving a sample of a microorganism inoculum diluted in a growth medium, wherein the or at least part of the compartments comprise respectively a single antimicrobial agent or a combination of antimicrobial agents, so that each inoculated compartment houses a respective test assay, wherein the incubation assembly is configured to provide an incubation and/or measuring environment of the one or more test assays in the one or more compartments,
   b) an interrogation and readout assembly configured to interrogate and readout the one or more test assays during incubation of the one or more carriers, wherein the interrogation and readout assembly is configured to facilitate i) measuring at least n times for each of the one or more test assays, with constant or inconstant frequency $f$ a signal derived from a chemical or physical property of the inoculated microorganism, wherein the signal represents an essentially monotonic function of the number of the microorganisms in the measured test assay, and ii) reading out corresponding values $\{x_i\}$ at corresponding recording times $\{t_i\}$, wherein i represents the index number of the measurement represented by an integer 1 to n, and wherein n represents a full integer of 13 or more measurements, and
   c) a computing assembly comprising one or more processors and one or more computer-readable media storing instructions that, when executed by the one or more processors, cause the one or more processors to perform operations comprising i) receiving from the interrogation and readout assembly the number n of readouts, the values $\{x_i\}$ and corresponding recording times $\{t_i\}$ and ii) estimating one or more slopes of linear trends $\alpha$ in data as a function of distribution of a difference from a subtraction of constituents of a pair of readout values $\{x_i\}$ and $\{x_j\}$, where j>i, divided by the time interval $\delta t_{ij}$ between taking readouts indexed i and j, whereby part or all of the n readout values $\{x_i\}$, but at least 13 or more readout values $\{x_i\}$ at corresponding recording times $\{t_i\}$ are used for the distribution, and iii) determining the qualitative or quantitative susceptibility of the inoculated microorganism against the single anti microbial agent or the combination of antimicrobial agents as a function of one or more slopes of linear trends $\alpha$.

10. The rapid antimicrobial susceptibility testing system according to claim 9, wherein the system is configured to facilitate simultaneous multi testing of the test assays in the one or more compartments.

11. The rapid antimicrobial susceptibility testing system according to claim 9, wherein the interrogation and readout assembly comprises an optical assembly, which is configured to interrogate and readout at least one of intensity of light, optical density, absorbance, turbidity, light reflection or other optical properties, conductivity, capacitance or other electrical properties; partial pressures of gases involved in metabolism of the microorganism, viscosity or nutrient uptake of the test assay during incubation.

12. The rapid antimicrobial susceptibility testing system according to claim 9, wherein the computing assembly is further configured to perform estimation and determination operations after each 10 measurements.

13. The rapid antimicrobial susceptibility testing system according to claim 9, wherein the computing assembly is further configured to estimate one or more slopes of linear trends $\alpha$ with a predetermined standard deviation $\sigma_\alpha$ by calculating the minimum number of readouts as a function of a standard deviation $\sigma$ of a high frequency noise of the measurement and time interval St between consecutive readouts.

14. A use of the rapid antimicrobial susceptibility testing system for performing a phenotypic antimicrobial susceptibility test (AST) using broth dilution according to claim 9 in determining qualitative and quantitative susceptibility of an inoculated microorganism.

15. The rapid antimicrobial susceptibility testing system according to claim 10, wherein the interrogation and readout assembly comprises an optical assembly, which is configured to interrogate and readout at least one of intensity of light; optical density, absorbance, turbidity, light reflection or other optical properties, conductivity, capacitance or other electrical properties; partial pressures of gases involved in metabolism of the microorganism, viscosity or nutrient uptake of the test assay during incubation.

16. The rapid antimicrobial susceptibility testing system according to claim 10, wherein the computing assembly is further configured to perform estimation and determination operations after each 10 measurements.

17. The rapid antimicrobial susceptibility testing system according to claim 10, wherein the computing assembly is further configured to estimate one or more slopes of linear trends $\alpha$ with a predetermined standard deviation $\sigma_\alpha$ by calculating the minimum number of readouts n as a function of a standard deviation $\sigma$ of a high frequency noise of the measurement and time interval St between consecutive readouts.

18. The rapid antimicrobial susceptibility testing system according to claim 11, wherein the computing assembly is further configured to perform estimation and determination operations after each 10 measurements.

19. The rapid antimicrobial susceptibility testing system according to claim 11, wherein the computing assembly is further configured to estimate one or more slopes of linear trends $\alpha$ with a predetermined standard deviation $\sigma_\alpha$ by calculating the minimum number of readouts n as a function of a standard deviation $\sigma$ of a high frequency noise of the measurement and time interval at between consecutive readouts.

20. The rapid antimicrobial susceptibility testing system according to claim 12, wherein the computing assembly is further configured to estimate one or more slopes of linear trends $\alpha$ with a predetermined standard deviation $\sigma_\alpha$ by calculating the minimum number of readouts n as a function of a standard deviation $\sigma$ of a high frequency noise of the measurement and time interval $\delta t$ between consecutive readouts.

\* \* \* \* \*